United States Patent [19]
Brown et al.

[11] Patent Number: 6,022,714
[45] Date of Patent: Feb. 8, 2000

[54] METHODS FOR ATTACHMENT OF A POLYNUCLEOTIDE TO A PRESELECTED MATERIAL

[75] Inventors: Eugene L. Brown, Newton Highlands; Joseph P. Dougherty, Somerville; Mary Collins, Natick, all of Mass.

[73] Assignee: Genetics Institute, Cambridge, Mass.

[21] Appl. No.: 08/574,860

[22] Filed: Dec. 19, 1995

Related U.S. Application Data

[63] Continuation of application No. 08/154,671, Nov. 18, 1993, abandoned, which is a continuation of application No. 07/911,446, Jul. 10, 1992, abandoned, which is a continuation of application No. 07/253,947, Oct. 3, 1988, abandoned, which is a continuation of application No. 06/729,700, May 2, 1985, abandoned.

[51] Int. Cl.$^7$ .......................... C07H 21/00; C07H 21/02; C07H 21/04; C12P 19/34
[52] U.S. Cl. .......................... 435/91.1; 435/6; 435/91.2; 435/91.3; 435/91.5; 435/91.51; 435/91.52; 435/810; 436/501; 536/22.1; 536/23.1; 536/24.1; 536/24.3; 536/24.31; 536/24.32; 536/24.33; 536/25.3; 935/16; 935/17; 935/77; 935/78; 935/88
[58] Field of Search .......................... 435/6, 91.1, 91.2, 435/91.3, 91.5, 91.51, 91.52, 810; 436/501; 536/22.1, 23.1, 24.1, 24.3–24.33, 25.3; 935/77, 78, 16, 17, 88

[56] References Cited

U.S. PATENT DOCUMENTS

| | | | |
|---|---|---|---|
| 4,711,955 | 12/1987 | Ward et al. | 536/29 |
| 4,828,979 | 5/1989 | Klevan et al. | 435/6 |

OTHER PUBLICATIONS

Smith et al. (1985) Nucleic Acid Research, vol. 13, No. 7, pp. 2399–2412.

*Primary Examiner*—Ardin H. Marschel
*Attorney, Agent, or Firm*—Testa, Hurwitz & Thibeault, LLP

[57] ABSTRACT

Compositions and methods for selectively linking a polynucleotide through its 5' or 3' end to one or more preselected materials such as insoluble matrices, solid supports, proteins, small molecular or labels are disclosed. Use of these compositions and methods in the production of diagnostic and affinity reagents are also disclosed.

5 Claims, 6 Drawing Sheets

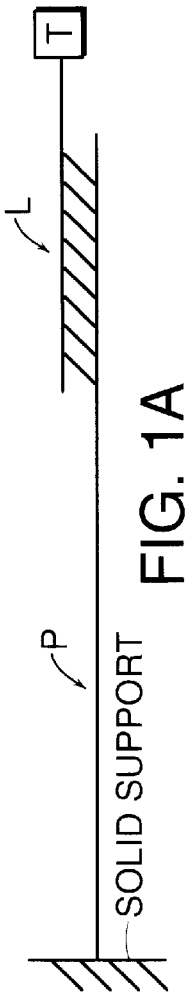
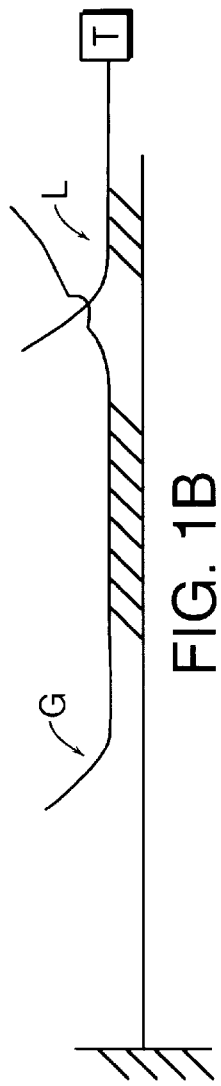
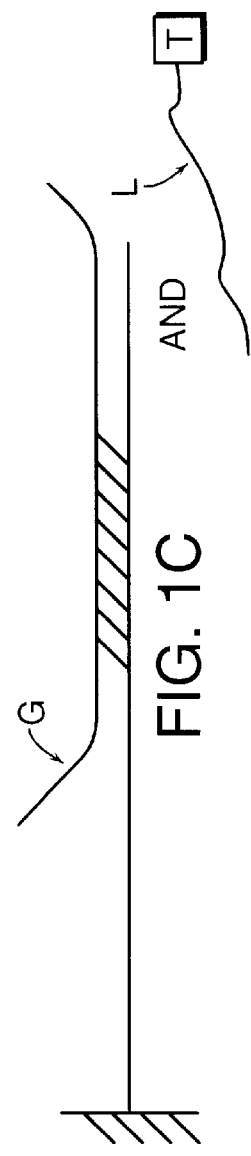

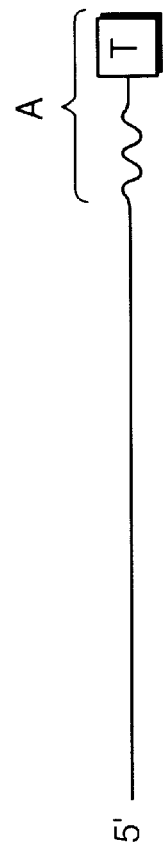
FIG. 4A
FIG. 4B
FIG. 4C
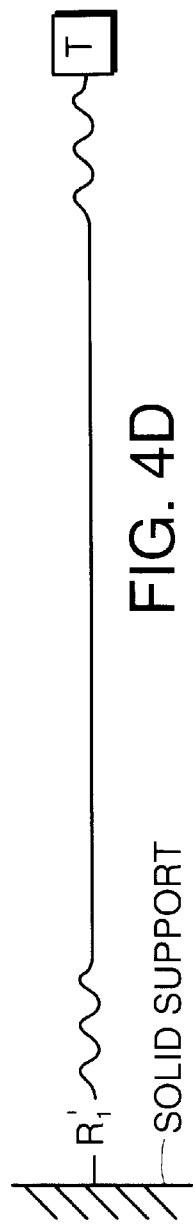
FIG. 4D

METHODS FOR ATTACHMENT OF A POLYNUCLEOTIDE TO A PRESELECTED MATERIAL

This is a continuation of application Ser. No. 08/154,671 filed on Nov. 18, 1993, now abandoned, which is an FWC of 07/911,446, filed Jul. 10, 1992, now abandoned, which is a continuation of 07/253,947, filed Oct. 3, 1998, now abandoned, which is a FWC of 06/729,700, filed May 2, 1985 now abandoned.

FIELD OF THE INVENTION

This invention pertains to compositions and methods for selectively linking a polynucleotide through its 5' or 3' end to one or more preselected materials such as insoluble matrices, solid supports, proteins, small molecules or labels and, particularly, to the use of said compositions and methods in the production of diagnostic and affinity reagents.

BACKGROUND OF THE INVENTION

In the field of recombinant DNA technology it is often desirable to bind covalently a polynucleotide to other materials such as insoluble matrices, solid supports, proteins, small molecules or labels. For example, a polynucleotide bound to a detectable label can be used in procedures for detecting the presence of a particular polynucleotide in a biological sample. A polynucleotide bound to an insoluble matrix or a solid support or one bound to a small molecule capable to binding to such a matrix or support is useful for affinity separation and purification of a specific polynucleotide from a biological sample. The binding of the polynucleotide may be direct as, for example, by reaction between chemical moieties on the label or the surface of the support and moieties of the polynucleotide. In addition to direct covalent binding, the polynucleotide may be indirectly attached to the label or support by a linking or adapter molecule.

A general approach for covalent attachment of a polynucleotide to an insoluble matrix or solid support involves attachment directly to the activated matrix or support without the intervention of a adapter molecule or extensor arm. For example, DNA has been directly attached to cyanogen bromide (CNBr) activated matrices such as agarose. (Arndt-Jovin, D. J., Jovin, T. M., Bahr, W., Frischauf, A-M. and Marquardt, M. *Eur. J. Biochem.* (1975) 54, 411–418.). These workers assume that coupling of the polynucleotide to CNBr-activated agarose under the conditions used involves direct multipoint attachment of the aromatic groups of the bases. DNA has also been directly coupled with CNBr-activated Sephadex. (Siddell, S. G., *Eur. J. Biochem.* (1978) 92, 621–629.). Another example of direct coupling of DNA to activated cellulose is provided by Biagioni et al. These workers have attached DNA to dichlorotriazinyl cellulose, most likely through the amino groups of adenine, guanine and cytosine (Biagioni, S., Sisto, R., Ferraro, A., Caiafa, P. and Turano, C., *Anal. Biochem.* (1978) 89, 616–619.).

In addition to direct covalent linkage, a variety of methods have been reported for the indirect covalent attachment of a polynucleotide to a matrix or support by means of a bifunctional molecule first attached to the matrix or activated support. Noyes et al. report the indirect coupling of DNA to cellulose which has been diazotized. The resultant diazotized aryl amine of the cellulose reacts primarily with guanine and uracil (thymine) residues of single strands (Noyes, B. E., and Stark, G. R., *Cell* (1975) 5, 301–310.). See also Seed, B., *Nucleic Acid Res.* (1982) 10, 1799–1810.

Another example of indirect, covalent attachment involves immobilization of polynucleotides to bisoxirane activated insoluble polysaccharides (Potuzak, H. and Dean, P. D. G., *Nucleic Acids Res.* (1978) 5, 297–303).

Alternatively, a polynucleotide may first be modified by a bifunctional molecule and subsequently attached to an insoluble matrix or solid support. For example, Dickerman et al. report derivatization of single-stranded DNA with 4-diazobenzoic acid and subsequent covalent attachment of the derivatized DNA to aminopentane Sepharose CL-4B (Dickerman, H. W., Ryan, T. J., Bass, A. I. and Chatterjee, N. K., *Arch. Biochem. Biophys.* (1978) 186, 218–234.). MacDougall, A. J., Brown, J. G., and Plumbridge, T. W., *Biochem. J.* (1980) 191, 855–858, describe the alkylation of double-stranded DNA with 4-bis (2-chloroethyl) amino-L-phenylalanine and immobilization of the resultant product of an insoluble support via the primary amino group of the phenylalanine moiety.

Each of the above methods of attaching a polynucleotide to a solid support, either directly or by first derivatizing the polynucleotide, has the significant disadvantage of reacting principally through the bases of the polynucleotide. The covalent linkages through the bases can be expected to interfere with the interactions of the immobilized polynucleotides with other macromolecules, particularly with hybridization reactions with other polynucleotides. This interference will be more severe for those hybridization reactions requiring a longer, uninterrupted region of free polynucleotide. Although the approach of the derivatizing a polynucleotide before subsequent immobilization allows greater control over the number of attachment points, covalent linkage is nonetheless through the bases of the polynucleotides.

Gilham has described direct attachment of polynucleotides to cellulose by a method involving specific activation of the terminal monosubstituted phosphate or polyphosphate of the polynucleotide by a water soluble carbodiimide. (Gilham, P. T., *Biochemistry* (1968) 7, 2809–2813.). The Gilham method is executed at pH 6 with an extremely large excess of the water soluble carbodiimide (present at greater than 200 mM), conditions under which the potential for base modification is increased. This potential for side reactions between carbodiimide and nucleotide bases or phosphodiester groups of the nucleotide backbone limits the utility of this approach. A similar scheme has been proposed by Urdea et al. (Urdea, M. S., Ghazi, H., Running J., Ku, L. and Warner, B. D., Poster Session; *DNA and RNA Probes: Strategies and Applications:* The Rensselaerville Institute Conference Center, Rensselaerville, N.Y.; Sep. 6–9, 1984.) in which 5' thiophosphate containing oligonucleotides are coupled with 2-bromoacetamide controlled pore glass. Although this method would be executed to provide some selectivity for the 5= end, attachment through the exocyclic amines is also possible. Moreover, low attachment yields are obtained.

Chu et al. have described a potentially simple method for attaching amines to the terminal 5'-phosphate of synthetic polynucleotides (Chu, B. C.. Wahl, G. M. and Orgel, L. E., *Nucleic Acids Res.* (1983) 11, 6513–6529.). The authors describe the coupling of uridine monophosphate to simple amines, polylysine and bovine serum albumin and the reaction of ethylene diamine with oligo(dT). The couplings are achieved by treating the 5'-phosphorylated species, either UMP or oligo(dT) with a water-soluble carbodiimide in imidazole buffer to form the corresponding 5'-phosphorimidazolide. The latter activated derivative is then isolated and treated with a large excess of amine to obtain a 5'-phosphoramidate. This chemistry requires a high concentration of amine to compete with water hydrolysis of the intermediate phosphorimidazolide. Because it is difficult to obtain relatively high concentrations of reactive amine groups on proteins and solid supports in an aqueous environment, very low levels of attachment, if any, will be achieved. If an immobilization takes place, a phosphoramidate bond is formed which is reported by Chu et al. to be unstable below pH 7.

van Boom et al. and Miyoshi et al. have described another immobilization chemistry for tethering 5'-spacer arm synthetic DNA. (Clerici, L., Campagnari, F., deRooij, J. F. M. and van Boom, J. H., *Nucleic Acids Res.* (1979) 6, 247–258; de Rooij, J. F. M., Wille-Hazeleger, G., Vink, A. B. J., and van Boom, J. H., *Tetrahedron* (1979) 35, 2913–2926; and (Miyoshi, K., Fuwa, T., European Patent Application, 0101985A1.). In this approach, synthetic DNA with an aliphatic amine spacer arm is reacted with a cyanogen bromide activated support, cellulose or agarose, and is reported to afford attachment only through the spacer arm's amine group. Although the coupling conditions are similar to those employed for immobilizing DNA through its exocyclic amines (see Arndt-Jovin et al., supra), Miyoshi and Fuwa argue that this form of attachment does not take place in their reaction scheme. They based their conclusions on the observation that DNA without the amine spacer arm did not show covalent linkage to activated cellulose or agarose. However, even though the initial attachment of DNA by their method is through the amine spacer arm, the likelihood of secondary attachment via the exocyclic amines of the nucleoside bases is increased once the DNA is attached and held in close proximity to the other activated sites on the support. Miyoshi and Fuwa report attachment of synthetic DNA per mg of support in the range of 0.1 to 0.3 nmole/mg.

A general method for covalently attaching DNA to enzymes has been disclosed by Renz. (Renz, M. and Kurz, C., *Nucleic Acids Res.* (1984) 12, 3435–3444.). The methods consists of first crosslinking the enzyme of interest to polyethyleneimine (PEI) with a crosslinking reagent, e.g., para-benzoquinone. This enzyme-PEI conjugate binds electrostatically to DNA via the PEI moiety and then can be covalently linked to single-stranded DNA with glutaraldehyde. It must be noted that this method is very cumbersome to execute, can be applied only to single-stranded DNA and, because attachment is through the DNA bases, would be expected to interfere with the hybridization reaction. In addition, cross linking an enzyme to PEI may significantly reduce its activity.

Several methods of covalent coupling of ferritin to the 3' terminus of RNA have been described. See Wu, M. and Davidson, N., *J. Mol. Biol.* (1973) 78, 1–21. In the simplest procedure a lysine amino group of the protein is coupled with the 3' terminal dialdehyde of the oxidized RNA and the resulting conjugate is stabilized by borohydride reduction. A second procedure modifies the protein with a —COCH$_2$Br group by acylation and attaches HSRCONHNH$_2$ to the 3' oxidized RNA by hydrazone formation. The protein and RNA are then coupled by reaction of the —COCH$_2$Br and —SH groups. In a third and preferred procedure the 3' terminus of the RNA is modified with a —NHCH$_2$CH$_2$SH group and then coupled to the —COCH$_2$Br acylated protein. These procedures as described are applicable only to RNA because they require an oxidizable 2', 3' diol terminus. In addition, two of the three procedures require that the protein be acylated before attachment, a step which will destroy the activity of some enzymes.

Chemical and enzymatic methods have been used to attach several types of small molecules to DNA. Pyrimidine triphosphates modified at the C-5 position to contain biotin have been incorporated into DNA with various polymerases and terminal transferase. (Langer, P. R., Waldrop, A. A. and Ward. D. C., *Proc. Natl. Acad. Sci. USA* (1981) 78, 6633–6637; Leary, J. J., Brigati, D. J., and Ward, D. C., *Proc. Natl. Acad. Sci. USA* (1983) 80, 4045–4049; Murasugi, A. and Wallace, R. B., *DNA* (1984) 3, 269–277.). The C-5 position of pyrimidines has similarly been used to attach an EDTA derivative in a chemically synthesized oligodeoxynucleotide (Dreyer, G. B. and Dervan, P. B. *Proc. Natl. Acad. Sci. USA* (1985) 82, 968–972.). This form of substitution at pyrimidines is known to destabilize DNA hybrids (Langer et al., supra). The enzymatic methods are expensive, difficult to scale up, and sometimes lead to uneven levels of incorporation of biotinylated nucleotides.

The chemical method of Chu et al., supra has been extended to permit the attachment of biotin (via an activated biotinyl ester, Chollet, A. and Kawashima, E. H., *Nucleic Acids Res.* (1985) 13, 1529–1541) and an EDTA derivative (Chu, B. C. F. and Orgel, L. E. *Proc. Natl. Acad. Sci. USA* (1985) 82, 963–967.) to the 5' end of synthetic oligodeoxynucleotide. These attachments contain the same phosphoramidate linkage as the prototype method of Chu et al., supra, and therefore presumably suffer similar instability at pH's below neutrality.

Phosphotriester methodology has been used directly to attach a biotin derivative to the 5' end of a synthetic oligodeoxynucleotide (Kempe, T. Sundquist, W. I., Chow, F. and Hu, S.-L., *Nucleic Acids Res.* (1985) 13, 45–57.). The instability of the amide linkage joining the biotin to the oligonucleotide to the normal conditions of DNA deprotection drastically limit the length and sequence of biotinylated oligonucleotides prepared by this method. The longest biotinylated oligonucleotide chemically prepared by Kempe et al., was five nucleotides (50 is routine in present art) and contained no adenosine or guanosine residues (these require stronger conditions for deprotection, which would break the link to biotin). An intercalating dye (acridine) has been covalently attached to the 3' end of oligothymidylic acids by phosphotriester methods. See Asseline, U., Delarue, M., Lancelet, G., Toulme, F., Thuong, N. T., Montenay-Garestier, T. and Helene, C., *Proc. Natl. Acad. Sci. USA* (1984) 81, 3297–3301. These compounds were used to study acridine intercalation between adenine and thymine base pairs.

Although the above procedures will attach polynucleotides to other materials, most have the disadvantage of not being highly selective for the 5' or 3' end of a polynucleotide. These procedures can provide multipoint attachment and hence may not leave the bases of the polynucleotide available for successful hybridization reactions. In addition, many of these procedures provide low yields of attachment and employ reactions conditions that are known to modify polynucleotides. Furthermore, many of these methods yield linkages which are not stable over long periods of time or outside of a narrow pH range. Thus, alternative methods for attaching polynucleotides to other substances are being sought. It is highly desirable to have a method for attaching polynucleotides to other substances which is highly specific for attachment at the 5' or 3' end of the polynucleotide.

SUMMARY OF THE INVENTION

The present invention provides compositions and methods for highly selective attachment of various substances to a polynucleotide through its 5' or 3' end. By using the compositions and methods of the present invention for attachment at only a single point, i.e., the 5' end or 3' end, the remainder of the polynucleotide chain is free to participate in interactions with other molecules, e.g. polynucleotides, proteins or organic dyes, in a manner similar to unmodified DNA.

The compositions of the present invention comprise a linking agent, an adapter molecule, a first and second polynucleotide, and a functionalized polynucleotide. The linking agent is attached to the first polynucleotide to form an adapter molecule which is then ligated to a second polynucleotide to form a functionalized polynucleotide.

The method of the present invention for attaching a polynucleotide to one or more preselected materials such as solid supports, insoluble matrices, proteins, small molecules on labels comprises the steps: (a) attaching a linking agent to a first polynucleotide to form an adapter molecule; (b) ligating the adapter molecule of step (a) with a second polynucleotide to form a functionalized polynucleotide; and (c) reacting the functionalized polynucleotide of step (b) with a preselected material. Alternatively, and preferably where the second polynucleotide is affected by the conditions of attachment of the adapter molecule to the preselected material, the adapter molecule is first attached to the preselected material and then ligated to the second polynucleotide. In a further alternative, where a desired attachment is to a small molecule which comprises a detectable group, affinity agent or hapten ligand stable to the conditions of steps (a) and (b), the small molecule may be made part of the linking agent.

The compositions and attachment methods of the present invention may be used in one or more ways in the production of diagnostic reagents for determining the presence of a target nucleotide sequence in the nucleic acid of a biological sample. For example, a probe polynucleotide, i.e., one capable of binding to a target nucleotide sequence, may include an adapter molecule attached thereto, so that the probe polynucleotide is immobilizable either before or after reaction with the target polynucleotide. One embodiment of the present invention provides a method for preparing diagnostic reagents that are based on the rapid displacement of a labelled polynucleotide from a probe polynucleotide by the target nucleotide sequence of a sample. This probe polynucleotide may be attached to a preselected material by means of an adapter molecule as described in the present invention. The probe polynucleotide of the reagent complex may be tagged by a second polynucleotide which contains a label and is bound by hydrogen bonds between purine and pyrimidine to the probe polynucleotide in a region that at least partially overlaps that to which the target binding sequence can bind. This labeled polynucleotide can itself be tagged by means of the adapter molecule of the present invention. Alternatively or in addition, an adapter molecule may be attached by the method of the present invention to said labeled polynucleotide to allow for immobilization or separation of the displaced labeled polynucleotide described above. In other embodiments the adapter molecule can serve as a labeled polynucleotide.

The present invention further includes a reagent for isolating and purifying nucleic acids and proteins from biological samples comprising an adapter molecule or a functionalized polynucleotide, as described above.

BRIEF DESCRIPTION OF THE DRAWINGS

FIG. 1:

FIG. 1A is a schematic view of one embodiment of a reagent complex useful in the rapid displacement of a labeled polynucleotide from a probe polynucleotide by the target nucleotide sequence of a sample. To the probe polynucleotide (p) (attached to a solid support) is hybridized the labeled polynucleotide (L) containing a tag (T).

FIG. 1B is a view similar to FIG. 1A in which the sample polynucleotide (G) is partially hybridized to the probe polynucleotide and has begun to displace the labeled polynucleotide.

FIG. 1C is a view similar to FIG. 1B in which the labeled polynucleotide has been fully displaced from the reagent complex.

FIG. 2:

FIG. 3:

FIG. 4:

FIG. 4A is a schematic view of a single-stranded polynucleotide with 5' and 3' ends indicated.

FIG. 4B is a view similar to FIG. 4A in which the single-stranded polynucleotide has been labeled with a 3' adapter molecule (A) containing a tag (T) bound via $R_1$.

FIG. 4C is a view similar to FIG. 4B in which a 5' adapter molecule (A) containing an $R_1$ group has been ligated to the single-stranded polynucleotide.

FIG. 4D is a view similar to FIG. 4C in which immobilization is achieved by a new bond ($R_1'$) between the labeled single-stranded polynucleotide and a solid support.

DETAILED DESCRIPTION OF THE INVENTION

Figure 2A:
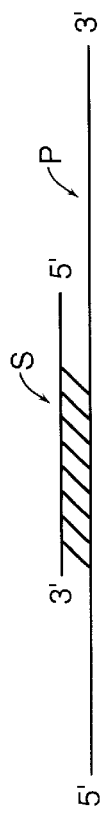
FIG. 2A is a schematic view of a cloned polynucleotide duplex suitable for labeling and immobilizing to prepare the reagent complex needed for the polynucleotide displacement assay shown in FIG. 1.

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3', 5'- phosphodiester linkages, and linked by carbon-nitrogen bonds at the 1-carbon of the sugar to pendant purine or pyrimidine bases such as, but not limited to, uracil (linked naturally to ribose only as rU), thymine (linked naturally to deoxyribose only as dT), cytosine (dC or rC), adenine (dA or rA) and guanine (dG or rG). Polynucleotides thus include strands of deoxyribonucleic acid (DNA) and strands of ribonucleic acid (RNA). The ends of such polynucleotide strands are referred to as the Five Prime (5') end, where the 5-carbon of the pentose is not linked to another pentose (but may bear hydroxyl, monophosphate or other natural or synthetic moieties), and the Three Prime (3') End, where the 3-carbon of the pentose is not linked to another pentose (but may similarly bear hydroxyl, monophosphate or other natural or synthetic moieties).

Complementary Base Pairing refers to the hydrogen bonding between opposite bases pendant on two polynucleotide strands, which is most energetically favorable for natural DNA when dG is opposite dC and dA is opposite dT. Bases other than the five naturally-prevalent bases adenine, cytosine, guanine, thymine and uracil also have preferential pairing: for example, 5-methylcytosine binds preferentially to guanine.

Hybridization is used herein to refer to admixing two polynucleotides under conditions conducive to the formation of double-stranded structures, with complementary base pairing causing such double-stranded structures to form where complementary sequences or nearly complementary sequences are present.

Ligation is the process for forming a phosphodiester bond between the 5' end of one DNA strand and the 3' end of another.

The basic components of the method of this invention are a linking agent, an adapter molecule, a first and second polynucleotide, a functionalized polynucleotide and one or more preselected materials such as insoluble matrices, solid supports, proteins, small molecules or labels. A linking agent is joined to a first polynucleotide to form an adapter molecule which is in turn joined to a second polynucleotide to form a functionalized polynucleotide. The preselected material may be attached to the adapter molecule before or after it is joined to the second polynucleotide or in some embodiments where the preselected material is a small molecule, the small molecule may be incorporated in the linking agent. In practicing this method where the first polynucleotide is synthesized, equipment for the synthesis is desirable.

The linking agents used in the present method are represented by formula I:

(I)

wherein $R_1$ is a functional group or a small molecule which comprises a detectable group, affinity agent, or hapten ligand joined by a stable linkage to $R_2$; n is an integer from 1 to 20; wherein $R_2$ is a suitable spacing group as described below; and wherein $R_3$ is a functional group which can react with the 5' or 3' hydroxyl of a polynucleotide to form a linkage stable to the conditions of polynucleotide synthesis and deprotection.

$R_1$ and $R_2$ must be stable under the conditions of making and using the compositions and reagents of the present invention and thus must be stable to the conditions of the chemistry of polynucleotide synthesis. (See e.g. *Oligonucleotide Synthesis, A Practical Approach*, M. J. Gait, Ed., IRL Press, 1984; Matteucci, M. D. and Caruthers, M. H., *J. Am. Chem. Soc.* (1981) 103, 3185–3195; Gait, M. J., Singh, M., Sheppard, R. C., Edge, M. D., Greene, A. R., Heathcliffe, G. R., Atkinson, T. C., Newton, C. R., Markham, A. F. *Nucleic Acids Res.* (1980) 8, 1081–1096; Itakura, K., Katagiri, N., Narang, S. A., Bahl, C. P., Marions, K. J., Wu, R. *J. Biol. Chem.* (1975) 250, 4592–4600; and Khorana, H. H. *Pure Appl. Chem.* (1968) 17, 349–381.). In some embodiments this may include protection of certain moieties during the preparation and use of the linking agent and later regeneration of these moieties.

The group $R_1$ is preferably a functional group or small molecule which survives or may be generated from a masked or latent form during or following polynucleotide synthesis and deprotection or storage. Some preferred final forms of $R_1$ may be incompatible with polynucleotides during long storage or may interfere with coupling the linking reagent to the first polynucleotide via $R_3$. In such cases it is desirable to mask the $R_1$ functionality or have it in a latent form so that it will be inert under the required conditions but may be revealed in its final reactive form at an appropriate time. For example, in those embodiments wherein $R_1$ is ultimately a carboxylic acid it is convenient to protect it, e.g. as its methyl ester, during the preparation and use of the linking reagent. This masked version of $R_1$ is converted to its final reactive form during the deprotection of the polynucleotide. Similarly, in those embodiments wherein $R_1$ is ultimately an aldehyde, this functionality may conveniently be kept in latent form as a vicinal diol or an alcohol. Both functionalities are protected, e.g. as acetates, during the preparation and use of the linking reagent. The acetate groups are removed in the normal course of polynucleotide deprotection. The aldehyde is generated just before use by, for example, the oxidation of the vicinal diol or enzymatic oxidation of the alcohol. Some forms of $R_1$, e.g. methyl or phenyl ketone, require no protection.

In some embodiments of this invention a preselected material may be a small molecule which comprises a detectable group or affinity agent stable to the steps of attaching the first and second polynucleotide. Under such circumstances, the small molecule may be included as one or more $R_1$ groups of the linking agent. In such embodiments the linking agent may also include one or more $R_1$ functional groups.

One example of such a linking agent which includes a biotin moiety linked by a stable ether linkage is 6-(biotinyloxy) hexyl 2-chlorophenyl 2-cyanoethyl phosphate which is illustrated below:

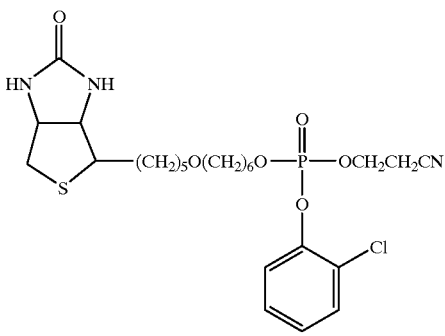

Some useful embodiments of this invention may include linking agents which contains several $R_1$ groups and may include both small molecules which comprises detectable or affinity groups as well as functional groups attached to branches of $R_2$. For example, immobilization of a polynucleotide to a support with a somewhat unstable surface might be facilitated by the use of a linking agent with several carboxylic acid $R_1$ functional groups attached to branches of $R_2$. In another embodiment a polynucleotide prepared with a linking agent containing a carboxylic acid functional group and a biotin moiety is immobilized on an amine-functionalized support via amide bond formation through the carboxylic acid group, cleaved from the support with an amidase, and ultimately recovered by binding to immobilized avidin through the biotin moiety. In yet another embodiment, a linker molecule with several biotin moieties is used to form a functionalized polynucleotide which can be detected at an enhanced level by reaction with several avidin-conjugated signal enzymes.

The number of $R_1$ moieties in a linking agent will vary depending on the type of $R_1$ and the ultimate use of the linking agent. For example, where $R_1$ is limited to a carboxylic acid functional group, and the linking agent is to be used to attach a polynucleotide to a solid support, n is preferably 1 to 6. Where $R_1$ is limited to aldehyde and the linking agent is used to attach a polynucleotide to a protein, n is preferably 1 to 4. Where $R_1$ is biotin and the linking agent is used to add biotin moieties to a polynucleotide n is preferably 1 to 20, more preferably 1 to 10. Of course, linking agents where $R_1$ is a single functional group or a single small molecule will be adequate for many purposes.

The arm, i.e. $R_2$, of the linking reagent is an aliphatic moiety. As used herein, aliphatic moiety shall mean an aliphatic hydrocarbon which may contain heteroatoms, aliphatic rings and aromatic rings. $R_2$ may be chosen for properties which include length, charge, rigidity, hydrophilicity and specific chemical cleavage (e.g., disulfide bond or 1,2-diol residues) and may include hydrocarbon arms, polyethylene glycol arms 2 to 300 monomeric units in length and arms of other inert oligomers. The arm may also contain units of unsaturation (e.g., double or triple bonds or aromatic or aliphatic rings) or heteroatoms (e.g., oxygen, nitrogen, sulfur, phosphorous, fluorine, chorine or bromine). $R_2$ must of course be stable to the conditions of polynucleotide synthesis and deprotection. In those embodiments of this invention where more than one $R_1$ group is present, $R_2$ must be branched at intervals to support the various $R_1$'s. $R_2$ may be a substituted or unsubstituted aliphatic hydrocarbon, preferably having from 1 to 30 atoms separating $R_3$ and the first $R_1$, more preferably 3 to 12. When a polyethylene glycol spacer is part of $R_2$ the arm contains 2 to 300 monomeric units; preferably 2 to 30. In those embodiments wherein the linking agent comprises two or more $R_1$ moieties, these moieties must be appropriately spaced along $R_2$. The optimal spacing will vary depending upon the intended application of the linking agent and the particular $R_1$ moieties. For example, in a linking agent containing several carboxylic acid functional groups which are to be used to immobilize a polynucleotide on a solid support, the spacing between each carboxylic acid functional group is 2 to 60 atoms, more preferably 4 to 30. Penta(methyl 1-levulinyloxy) dipentaerythrityl 2-chlorophenyl 2-cyanoethyl phosphate which is illustrated below, is an example of a polycarboxylic acid linking agent.

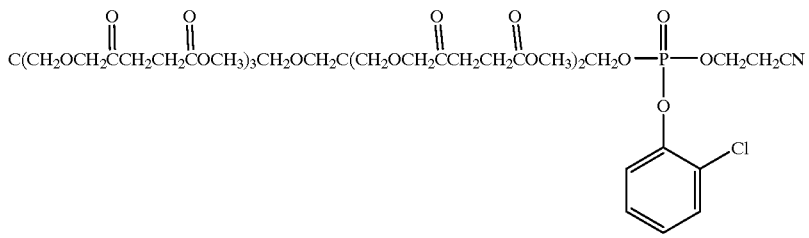

In an embodiment with several biotin moieties which will be used to immobilize a polynucleotide on an avidin support, it may be preferable to have the biotin moieties separated from one another by at least 12 atoms to allow each biotin full interaction with separate avidin partners.

In some embodiments of this invention it is desirable to have a means by which the linkage formed between a polynucleotide and a chosen substance may be broken quantitatively to release the polynucleotide without modification of the polynucleotide. Two general solutions to this problem are available, both of which involve the inclusion in the linkage of a cleavable group not found in the polynucleotide. In the first solution a cleavable group such as a disulfide or vicinal diol is included as part of $R_2$, i.e. built into the linking agent. In the second case, $R_1$ is chosen so that it reacts with the preselected material to form a bond cleavable by a specific chemical or enzymatic process. For example, when $R_1$ is a carboxylic acid it can be reacted with a material containing amine moieties to form an amide linkage which can later be cleaved by an amidase without reaction with the polynucleotide.

$R_3$ is any functional group which will react with the 5' or 3' hydroxyl of the first polynucleotide to form a bond stable to the deprotection conditions of polynucleotide synthesis. The functional group $R_3$ is a substituted alkyl or aryl sulfonate such as tosylate, a halide, or more preferably a phosphonate, phosphinylating group or a phosphorylating group.

When $R_3$ is a phosphorylating or phosphinylating group it is represented by the formula:

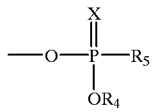

$R_4$ is preferably a methyl, cyanoethyl, or chlorophenyl moiety or other residue that can be selectively cleaved at a later stage of the attachment scheme. $R_5$ is a ligand that is usually removed to afford a very reactive linking reagent. Preferred ligands when the first polynucleotide is prepared by phosphite synthesis chemistry include morpholine and N,N-diisopropyl amine. In phosphotriester synthesis chemistry, $R_5$ is preferably —OCH$_2$CH$_2$CN. When X is a pair of electrons, $R_3$ is a phosphinylating group; when X is an oxygen or sulfur atom, $R_3$ is a phosphorylating group.

In the preferred linking agents, $R_1$ is carboxylic acid, ketone or aldehyde; $R_2$ is as described above; and $R_3$ is a phosphinylating or phosphorylating group.

Examples of linking agents of formula (I) include 12-methylcarboxydodecylmethyl-N,N-diisopropylphosphoramidite, 5-oxohexylmethyl-N,N-diisopropylphosphoramidite, 12-phenyl-12-oxododecylmethyl-N-morpholinophosphoramidite, 12-methyl-11,12-diacetyltridecanediol methyl N-morpholino phosphoramidite, 12-methylcarboxydodecyl 2-chlorphenyl 2-cyanoethyl phosphate, 6-(biotinyloxy) hexyl 2-chlorophenyl 2-cyanoethyl phosphate and penta (methyl 1-levulinyloxy) dipentaerythrityl 2-chlorophenyl 2-cyanoethyl phosphate.

The linking agents of the present invention can be prepared from available starting materials using methods well known in the art. Organic acids, ketones or aldehydes selected to have a hydroxyl substituent capable of reacting with a halo-(2° amino)- phosphine to form a phosphoramidite are useful in forming the linking agents of this invention and can be prepared using conventional techniques of organic synthetic chemistry. See, for example, Beaucage, S. L. and Caruthers, M. H., *Tetrahedron Lett.* (1981) 22, 1859–1862; Matteucci et al., supra,. Halo-(2° amino) phosphines useful for this invention include halo-(2° amino) alkyl-, aryl- or aryloxyphosphines. Halo is preferably either chloro or bromo. Preferred halo-(2° amino) phosphines include chlorodiisopropylaminomethoxyphosphine, N-morpholinochloromethoxyphosphine, chlorodiisopropylamino (cyanoethoxy)phosphine and N-morpholinochloro (cyanoethoxy) phosphine.

Hydroxyl containing organic acids, ketones or aldehydes masked or unmasked are also capable of reacting with mono or diesters of phosphorous oxychloride or their bistriazole derivatives to form a phosphotriester linking agent. When reagent preparation is executed with a monoester phosphorylating reagent, a second ligand such as β-cyanoethyl is added after the hydroxyl containing acid, ketone or aldehyde has been added (See e.g., Itakura et al. supra). When the phosphorylating agent is a diester one ligand is usually the second ligand mentioned above. Preferred reagents include 2- or 4- chlorophenyl phosphorodi(triazolide) and 2- or 4- chlorophenyl-β-cyanoethyl phosphorotriazolide.

The adapter molecules of the present invention are represented by the general formula II:

$$(R_1)_nR_2R_6R_7 \quad (II)$$

wherein, $R_1$, n and $R_2$ have the same meaning as in (I) above. $R_6$ represents the linkage formed between the linking agent and the first polynucleotide and may be an ether ($R_2$—O—$R_7$), a phosphonate

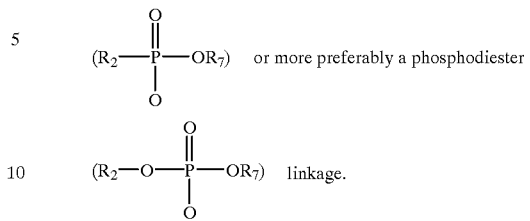

$R_7$ is a single stranded polynucleotide having 4 to 200 nucleosides, preferably 6 to 100 nucleotides, and more preferably 11 to 50 nucleotides. In the particularly preferred adapter molecules $R_1$, n and $R_2$ are as described above; $R_6$ is a phosphodiester linkage and $R_7$ is an polynucleotide having 11 to 50 nucleosides wherein the pentose moieties are preferably deoxyribose.

The functionalized polynucleotides of the present invention are represented by the formula III:

$$(R_1)_nR_2R_6R_7R_8 \quad (III)$$

wherein $R_1$, n, $R_2$, $R_6$, and $R_7$ have the same meaning as set forth above and wherein $R_8$ is a second polynucleotide joined by a phosphodiester linkage to $R_7$.

The second polynucleotide, $R_8$, of the present invention may be single-stranded, or partly or completely double-stranded. It may include naturally occurring DNA, cDNA, RNA, DNA-RNA, or a synthetic polynucleotide. In some embodiments, $R_8$ may itself be formed by the ligation of two or more polynucleotides. The particular $R_8$ will depend on the intended application of the functionalized polynucleotide, but sequences can be chosen for such properties as complementary to a desired "target" sequence, presence of restriction enzyme recognition sites, or the presence of other polynucleotide binding sites. Other sequences may also be part of $R_8$ which, while not themselves directly involved in binding macromolecules, may serve other useful functions, e.g. to provide spatial separation from supports or labels over and above that provided by $R_2$.

The phosphodiester linkage between $R_7$ and $R_8$ is typically formed enzymatically, and any of the methods known in the art are useful in the practice of the present invention. These include blunt or sticky end or splint-mediated ligations, and may involve the use of RNA or DNA ligase, as appropriate. The functional groups chosen for $R_1$ will depend upon the nature of the preselected material to which it is to be attached. Preferably $R_1$ is ketone, —COOH or aldehyde. These three terminating functional groups have a spectrum of reactivity with nucleophiles, e.g., alcohols, thiols, phenols, amines, hydrizines and hydrazides.

A carboxylic acid adapter molecule or functionalized polynucleotide, activated with a carbodiimide, is a preferred reagent for forming a covalent bond between the 5' or 3' end of a polynucleotide and a small molecule. Attachment of many kinds of small molecules to an adapter molecule or a functionalized polynucleotide may be carried out rapidly and easily with the carboxylic acid versions of the polynucleotides activated by, e.g., carbodiimides or isoxazolium salts. This procedure is most appropriate for those small molecules which contain or which may easily be derivatized to contain nucleophilic functional groups as described above. However, certain small molecules may be affected adversely by the activation reagents for carboxylic acids. For those small molecules which are so affected and which contain or may be modified to contain nitrogen nucleophiles, attachment of a ketone or aldehyde adapter molecule or functionalized polynucleotide via a reductive amination procedure is preferred. Examples of such sensitive functional groups include carboxylic acids and thiols. Solid supports may often be modified to obtain desired surface functionalities. The carboxylic acid and ketone adapter molecules have been reacted with a variety of nucleophiles, e.g. aromatic and aliphatic amines, hydrazides (including brotin hydrazide), and hydrazine. These reactions serve as models for demonstrating the reactivity of the various electrophilic $R_1$'s with nucleophilic functional groups typically encountered in useful small molecules as well as solid supports. Biotin hydrazide also has intrinsic utility as an anchoring group. See Bayer, E. A. and Wilchek, M., *Methods Biochem. Anal.* (1979), 26, 1–45.

For bond formation with a protein, e.g. an enzyme, a ketone or aldehyde adapter molecule or functionalized polynucleotide and mild reducing agent such as $NaCNBH_3$ is a preferred choice because most proteins are not chemically modified by mild borohydride reducing reagents as they are by carbodiimides.

The base of each nucleoside is typically selected from the group consisting of adenine, guanine, cytosine, thymine or uracil. As discussed more fully below, in certain embodiments of this invention the polynucleotide of the adapter molecule can include sequences deliberately selected for specific properties such as the presence of a unique restriction enzyme site, complementarity to a desired sequence, i.e. a probe or a target polynucleotide, or affinity for another material. The polynucleotide portion of the adapter molecule can be made from available starting materials and by methods well known in the art. See, for example, Gait, supra; Matteucci et al., supra; Beaucage et al. supra; Ti, G. S., Gaffney, B. L., and Jones, R. A., *J. Am. Chem. Soc.* (1982) 104, 1316–1319; and Crockett, G. C., Aldrichchimica Acta (1983) 16, 47–55, Aldrich Chemical Company, Inc. The synthesis of a desired polynucleotide may also be carried out in a commercially available automated DNA synthesizer.

During polynucleotide synthesis certain reactive moieties on the nucleotides are protected by avoid undesirable side reaction. Any of the protecting groups known to those skilled in the art are useful in the practice of the present invention. See, e.g., Matteucci et al.; Ti, et al.; and Crockett, all supra.

The adapter molecules (II) of the present invention are preferably formed by condensing a selected linking agent (I) with a fully protected polynucleotide which can be synthesized as described above. This procedure is easily adapted to automated polynucleotide synthesis. The crude adapter molecule may be purified by conventional methods such as reverse phase HPLC, (Fritz, H. J., Belagaje, R., Brown, E. L., Fritz, R. H., Jones, R. A., Lees, R. and Khorana, H. G. *Biochemistry* (1978) 17 1257–1267.).

While the method of the present invention is not limited with regard to the spacings between the point of attachment of the adapter molecule to a support and the polynucleotide portion of the adapter molecule and/or region of the second polynucleotide which binds specifically to a target nucleotide sequence, it is preferably that this spacing be sufficiently large for the hybridization between target nucleotide sequence and target binding region of the polynucleotide portion to occur such that the target binding region of the polynucleotide portion has maximal freedom of movement during hybridization. Ligation and hybridization techniques are well known in the art. Ligation may be accomplished by several well known enzymatic techniques, including blunt or sticky-end as well as splint-mediated ligation. Reaction conditions that promote hybridization are well known to those skilled in the art. See, e.g., Maniatis et. al. *Molecular Cloning, a Laboratory Manual*, Cold Spring Harbor (1982).

In embodiments other than wherein $R_1$ is itself a preselected material or wherein $R_1$ is an affinity agent or hapten ligand, the means of attachment of the adapter molecule to the preselected material is some form of specific covalent attachment of $R_1$ effected through conventional chemical techniques. In those embodiments wherein $R_1$ is an affinity agent or hapten ligand, attachment of $R_1$ to the preselected material is by some form of specific biochemical affinity between $R_1$ and the preselected material, e.g. biotin-avidin or antigen-antibody.

The $R_1$ group of the adapter molecule can be attached to the preselected material, at any time i.e. prior to ligation to a second polynucleotide, after ligation to a second polynucleotide or after hybridization of the second polynucleotide to a target polynucleotide. Preferably, where a second polynucleotide is involved which is affected by the conditions of attachment, the adapter molecule is first attached to the preselected material and then ligated to the second polynucleotide.

The solid support on which the adapter molecule is immobilized in certain embodiments may be of almost any conventional type, including especially polymeric materials, ceramic materials, walls of a test tube or other container, paper, nitrocellulose felts, fibers, or glass. In some forms of the invention, the solid phase consists of particles, beads or fibers made of materials such as polysaccharides, protein, polystyrene, latex, polyamide or glass. In other forms of the invention, such particles or beads may be metal oxides such as titanium dioxide, zinc or oxide or magnetite. See e.g., European Application No. 0 113 452 and Matijevic, E., *Acc. Chem. Res.* (1981) 14, 22–29. Polysaccharides such as cellulose, agarose and dextran and polystyrenes in the form of both porous and nonporous beads are widely used for immobilization.

Solid supports, e.g. latex particles that contain primary amines, hydrazides and hydrazines, are preferred for covalent bond formation with the carboxylic acid adapter molecules and functionalized polynucleotides of the present invention. In other equally preferred embodiments of the invention, the adapter molecule is not immobilized to a support but is in solution and $R_1$ is a small molecule or is covalently attached to a small molecule such as an affinity reagent, (e.g., biotin), or a chemical moiety, (e.g., a chemical hapten such as a dinitrophenyl derivative) so as to be ultimately immobilizable or separable, if desired, after ligation with a second polynucleotide and hybridization with a target polynucleotide, e.g., by passing through a porous bed or filter with strepavidin on a support or by immunoprecipitation. As discussed more fully below, such immobilizaiton will separate hybridized polynucleotides for subsequent determination.

In some embodiments, $R_1$ of the adapter molecule is a detectable group or is used to attach a group or label, susceptible to detection, to the second polynucleotide. Directly detectable tags which may be used to label the adapter molecule include radioactive nuclides (especially phosphorous-32, sulfur-35, carbon-14 or iodine-125 labeling of the nucleotides of the adapter molecule), fluorescent compounds (such as fluorescein or rhodamine derivatives attached to $R_1$ of the adapter molecule or to one or more of the unpaired bases of the adapter molecule or fluorescent polymer beads) or moieties detectable by other means (including being cleaved off) such as the moiety dinitrophenol which can be subsequently detected colorimetrically or by other means.

Indirectly detectable tags for the adapter molecule include those modifications that can serve as antigenic determinants, affinity reagents, antigens or antibodies recognizable through immunochemical or other affinity reactions such as described in EPA 63,879, WO 83/02277 and EPA 97,373. Other indirect tags include proteins, e.g. enzymes, polymers of enzymes or protein-enzyme conjugates, including alkaline phosphatase, horseradish peroxidase, or β-galactosidase whose presence can be determined by addition of the substrate for the enzyme and quantification of either the enzymatic substrate or, preferably, the enzymatic product. Similarly, the tag may be an apoenzyme, co-enzyme or zymogen, enzymatic modifier or the like, with the other necessary reagents usually added with the appropriate enzymatic substrate. The adapter molecule may also be attached to signal molecules such as fluorochromes, chemiluminescence precursors or latexes (Schall, R. F. and Tenoso, H. J. *Clin. Chem.* (1981) 27, 1157–1164.). Release tags in the form of gas-phase electrophores are also examples of signal molecules. See Joppich-Kuln, R., Joppich, M. and Giese, R. W., *Clin. Chem.* (1982) 28, 1844–1847.

The adapter molecule and method of the present invention will be useful in any procedure which involves linking a polynucleotide to one or more preselected materials such as insoluble matrices, solid supports, proteins, small molecules or labels. The method described herein permits attachment by a variety of bonds (e.g. an amide or ester bond) not found in DNA and thus permits DNA release by a chemical or enzymatic (for example, amidase) cleavage step. In addition the adapter molecule provides a spatial separation of the DNA from the solid support which increases its accessibility to macromolecules, e.g., DNA, RNA and proteins. The reagents of this invention are thus widely useful to prepare diagnostic reagents for use in the field of biomedical research and recombinant DNA technology, including but not limited to, affinity chromatography and diagnostic assays. For example, the adapter molecule of the present invention may be used in a diagnostic assay either to immobilize a polynucleotide or to provide a detectable level on a polynucleotide or both. In other words, in some procedures a first adapter molecule may be used for labeling and a second adapter molecule for immobilization.

The adapter molecule and method of the present invention is useful in a diagnostic assay technique, described in U.S. patent application Ser. No. 652,218 which is incorporated herein by reference, for the identification of a particular biological species or medical condition by detecting cleavage at a predetermined restriction endonuclease cleavage site, if present, in a biological sample or analyte, said method comprising:

(a) mixing the analyte, under hybridization conditions, with a labelled single-stranded polynucleotide ("probe polynucleotide") capable of forming a specific double-stranded hybrid with analyte polynucleotide ("target polynucleotide"), said hybrid containing a predetermined restriction endonuclease cleavage site; (b) allowing sufficient time for any hybridization reaction to occur between the analyte and the labelled single-stranded polynucleotide;

(c) digesting any hybrid double-stranded polynucleotide formed in step (b) with a predetermined restriction endonuclease, specific for said predetermined restriction site formed in step (b);

(d) separating the resulting labelled cleaved polynucleotide fragments from uncleaved labelled single-stranded polynucleotide and other uncleaved fragments; and (e) determining the presence of the predetermined cleavage site by measuring the amount of double-stranded cleaved labelled fragments present and thereby determining the presence of the biological species or condition.

In the restriction endonuclease cleavage site assay described above it may be desirable to label the probe polynucleotide with a 3' adapter molecule and immobilize said polynucleotide with a 5' adapter molecule or vice versa. In this way the liquid phase containing double-stranded cleaved labelled fragments may be separated from the solid phase containing bound uncleaved hybrid polynucleotide. It may also be desirable initially to have the tagged polynucleotide in solution and treated after the hybridization to the target polynucleotide so that only those labelled polynucleotide fragments released from the tagged polynucleotide/target polynucleotide hybrid via digestion with the restriction enzyme remain in the liquid phase for subsequent determination. Such separation of the solid phase containing bound hybrid polynucleotide from liquid phase containing cleaved labeled polynucleotide may be by physical means such as chromatography, filtration, centrifugation, decantation or magnetic or electric field.

The adapter molecule and method of the present invention is also useful in a method, described in co-pending U.S. patent application Ser. No. 607,885 (See FIGS. 1A–1C) which is incorporated herein by reference, for determining the presence of a predetermined target nucleotide sequence (either DNA or RNA) in the nucleic acid of a biological sample which comprises the steps:

(a) providing a reagent complex of (i) a probe polynucleotide which is capable of base pair binding via hydrogen bonds of purine/pyrimidine base pairs to the target nucleotide sequence, and (ii) a labeled polynucleotide which is bound by base pair binding via hydrogen bonds of purine/pyrimidine base pairs to the probe polynucleotide in a region of the probe polynucleotide at least partially coextensive with the region in which the probe polynucleotide is capable of binding to the target nucleotide sequence;

(b) contacting the reagent complex with a sample under conditions in which the target nucleotide sequence, if present, binds to the probe polynucleotide and displaces labeled polynucleotide from the reagent complex; and (c) determining the presence (which can include, of course, determining the amount) of labeled polynucleotide displaced from the reagent complex. The amount displaced can be determined indirectly by determining the amount of the labeled polynucleotide remaining in the reagent complex. The label serves as a reliable and quantitative measurement functionally related to the presence and concentration of the target nucleotide sequence in a sample.

In practicing the aforementioned method of U.S. Ser. No. 607,885, the attachment method of the present invention may be used in one or more ways in the production of reagents. For example, it may be desirable initially to immobilize the reagent complex on a solid support so that the liquid phase containing displaced labeled polynucleotide may be separated from the solid phase containing bound complex (See FIG. 1A). It may also be desirable initially to have the reagent complex in solution, execute the displacement step and then attach complexes still present (and other forms of probes including those hybridized to a target nucleotide sequence) to a solid support, followed by a similar solid/liquid separation. In some instances, the reagent complex may be manufactured directly in the duplex form and then be immobilized to the solid support via the adapter molecule. The adapter molecule of the present invention may be useful for mediating or participating in such attachment as described above. In either case, i.e. where the reagent complex is immobilized before or after displacement, the means of attachment of the probe polynucleotide to the solid phase may be by indirect linkage to the solid support by means of the adapter molecule of the present invention.

The probe polynucleotide may further be linked by means of the adapter molecule of the present invention wherein the $R_1$ moiety of the adapter molecule (II) is an affinity agent or is reacted with an affinity reagent, such as biotin, which may then be reacted with the support. For example, the adapter molecule may be ligated to the 5' or 3' end of the probe polynucleotide and $R_1$ is biotin or $R_1$ is chemically modified, either before or after ligation, to contain a biotin moiety which can then be reacted with a solid support containing avidin moieties.

The labeled polynucleotide of the aforementioned methods has a label susceptible to detection, especially after displacement. The adapter molecule of the present invention may be used to attach said label, particularly in cases where the label is located at one end of the labeled polynucleotide. The adapter molecule of the present invention may also be used directly as the labeled polynucleotide.

Multiple tags can be added in manufacturing the labeled polynucleotide such as with a terminal deoxynucleotidyl transferase enzyme. Multiple labeled polynucleotides, e.g., one containing the enzyme (or apoenzyme) and one containing the coenzyme, may also be used. One form of attachment of the enzyme to the labeled polynucleotide is through affinity reagents, e.g., strepavidin/biotin, which have been previously attached to the labeled polynucleotide by means of the adapter molecule and method of the present invention as described above. Such form could be used in embodiments wherein, for example, the reagent complex is prepared by hybridizing a biotin-labeled polynucleotide to the probe and then binding strepavidin-enzyme to the biotin prior to the displacement step. Most forms of tags, especially if remote from the pairing region of the labeled polynucleotide, will have little effect on the strength of base pairing between the labeled polynucleotide and the target or probe polynucleotide. Some forms of labeling, such as covalently bound biotin on nucleotides of the labeled polynucleotide in the pairing region and such as a large enzyme molecular or fluorescent moiety linked to nucleotides in or near the pairing region, may have an appreciable effect on reagent complex stability. Such effect generally could be to destabilize the labeled polynucleotide/probe polynucleotide binding. It can be seen that the adapter molecule and method of the present invention may be useful in selectively tagging the labeled polynucleotide in a region remote from the base pairing region, and thus ameliorating any destabilization.

Figure 2B:
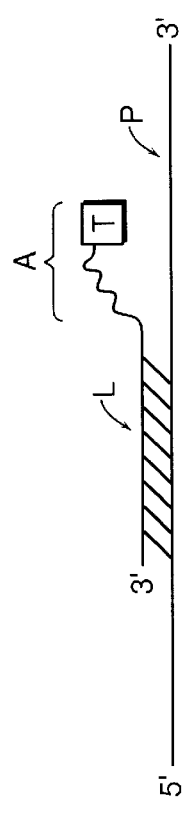
FIG. 2B is a view similar to FIG. 2A in which a 5' adapter molecule (A) containing a tag (T) covalently bound via $R_1$ has been ligated to a signal polynucleotide (S) to form the labeled polynucleotide (L).
Figure 2C:
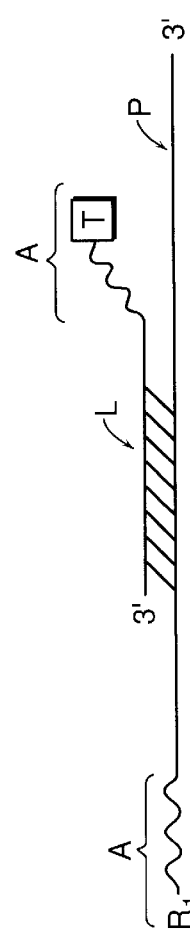
FIG. 2C is a view similar to FIG. 2B in which a 5' adapter molecule (A) containing an $R_1$ group has been ligated to the probe polynucleotide.
Figure 2D:
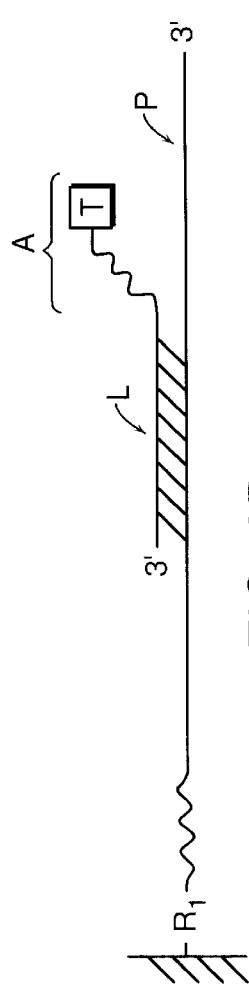
FIG. 2D is a view similar to FIG. 2D in which attachment is achieved by a new bond ($R_1'$) between the probe polynucleotide and a solid support.

Two of several approaches available for labeling and immobilizing the reagent duplex needed for the polynucleotide displacement assay, i.e. method of U.S. Ser. No. 607,885, are shown in FIGS. 2 to 3. The first one shown in FIG. 2 starts with a cloned duplex comprising a probe polynucleotide (P) and a signal polynucleotide (S) FIG. 2A) and attaches to the 5' end of the signal polynucleotide by DNA ligase an adapter molecule (A) wherein $R_1$ is a detectable group (T) or has a label or detectable group (T) bound via $R_1$ to form a labeled polynucleotide (FIG. 2B). In a second step, a second adapter molecule, this one containing an $R_1$ functional group is attached via DNA ligase to the probe polynucleotide (FIG. 2C). Lastly, this functional group is utilized to form a bond with a solid support (FIG. 2D). In this scheme the label and the solid support are distal to each other. One variation on this scheme utilizes a 3' adapter molecule for labeling the signal polynucleotide and provides a reagent complex in which the label and solid support are proximal to each other. Another variation changes the order in which the steps are executed. Such approaches based upon a cloned duplex are described in more detail in a commonly assigned patent application filed concurrently herewith, E. F. Fritsch and M. Collins inventors, Attorney's Docket 50-203, which is hereby incorporated by reference.

Another way to prepare the reagent complex is to start with two pieces of single-stranded DNA as shown in FIG. 3. In this procedure the adapter molecule wherein $R_1$ is a detectable group or has a label or detectable group attached via $R_1$ is ligated to the signal polynucleotide to form the labeled polynucleotide.

Figure 3A:
FIG. 3A is a view similar to FIG. 2A. However, the probe polynucleotide (P) does not have the signal polynucleotide hybridized to it.
Figure 3B:
FIG. 3B is a view similar to FIG. 2C in which the probe polynucleotide does not have the labeled polynucleotide hybridized to it.
Figure 3C:
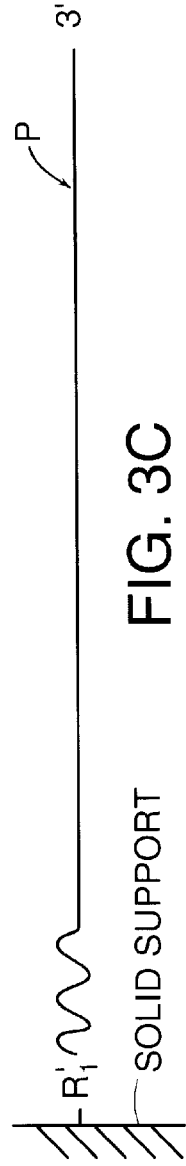
FIG. 3C is a view similar to FIG. 2D in which the probe polynucleotide does not have the labeled polynucleotide hybridized to it.
Figure 3D:
FIG. 3D is a view identical to FIG. 2D in which the reagent complex has been formed by mixing the labeled polynucleotide (L) with the immobilized polynucleotide (P) under conditions which allow hybridization.

Separately, the probe polynucleotide (FIG. 3A) is modified with an adapter molecule containing $R_1$ (FIG. 3B) and then immobilized to a solid support (FIG. 3C). Lastly, an excess of the labeled polynucleotide is added, the formation of the duplex takes place using hybridization conditions (FIG. 3D) and the excess of unbound labeled polynucleotide is washed away.

The scheme shown in FIG. 4 is specific for preparation of reagents needed for the restriction endonuclease cleavage site assay, i.e. method of U.S. Ser. No. 652,218. In this procedure one single-stranded polynucleotide is modified with a 5' and 3' adapter molecule and then attached through the 5' end. Attachment is equally possible through the 3' end.

Thus, we have described and provided examples of a novel scheme for attachment of a polynucleotide to one or more preselected materials, such as an insoluble matrices, solid supports, proteins, and small molecules.

This invention will be further understood with reference to the following examples which are purely exemplary in nature and are not meant to be utilized to limit the scope of the invention.

EXAMPLES

The abbreviations usesd herein are defined below:

The abbreviations for deprotected oligonucleotides are according to IUPAC-IUB Commission on Biochemical Nomenclature Recommendations (*J. Biol. Chem.* (1970) 245, 5171–5176) while those for protected compounds are based on the suggestions of Reese (Reese, C. B., *Nucleic Acids Res.* (1980) 8, 2039–2053). Accordingly, 6-N-benzoyl-2'-deoxyadenosine, 2-N-isobutyryl-2'-deoxyguanosine and 4-N-benzoyl-2'-deoxycytidine are represented by the italicized letters A, B and C, respectively. Phosphate residues which are protected by a methyl group (phosphite method) or 2-chlorophenyl residues (phosphotriester method) are represented by the italicized letter p. Attachment of synthetic DNA to controlled pore glass by standard chemistry is represented by: cpg. DEC is the abbreviation for 1-ethyl-3-(3-dimethylaminopropyl) carbodiimide.

Reagents

Diisopropylethylamine and triethylamine were distilled from p-toluenesulfonyl chloride and calcium hydride and stored in the dark over 4 angstrom molecular sieves under argon. Chlorodiiso-propylaminomethoxyphosphine and chloromorpholinomethxoxy phosphine were obtained from American BioNuclear. The morpholino compound was distilled in vacuo before use ($^{32}$P NMR: delta 171 with less than 5% delta 13 after distillation). Reagent grade methylene chloride was stored over 4 angstrom molecular sieves and alumina and sparged with argon before use to remove dissolved oxygen. For high performance liquid chromatography (HPLC) gradients of 0.1M triethylammonium acetate (pH7) and acetonitrile as well as Ultrasphere ODS™ columns (5 um particle size) obtained from Beckman Instruments were employed throughout.

Example I

Preparation of 12-Methylcarboxydodecylmethyl N, N-diisopropyl Phosphoramidite

12-Methylcarboxydodecyl methyl N,N-diisopropyl phosphoramidite is illustrated below:

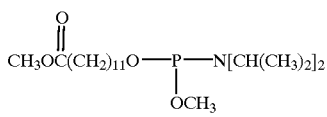

A. Esterification of 12-hydroxydodecanoic acid

12-Hydroxydodecanoic acid (10.82 g, 50 mmol) was added to 3% HCl in CH$_3$OH (210 ml). The reaction was stirred at 22° C. for 3.5 hours and concentrated on a rotary evaporator. The residue was taken up in ethyl acetate (200 ml) and washed with 1M K$_2$CO$_3$ (2×150 ml), and once with saturated aqueous NaCl (150 ml), dried over Na$_2$SO$_4$, concentrated and vacuum distilled to yield 10.3 g of methyl 12-hydroxydodecanoate in 90% yield; mp 33.5–35.0° C., $^1$H NMR (CDCl$_3$) delta 3.66 (s, 3H), 3.62 (t, 2H), 2.88 (t, 2H), 1.28 (br s, 18H).

B. 12-Methylcarboxydodecyl methyl N,N-diisopropylphosphoramidite

To a rapidly stirred solution of diisopropylethylamine (3.4 ml, 19.5 mmol) and chlorodiisopropylaminomethoxyphosphine (2 ml, 9.75 mmol) in CH$_2$Cl$_2$ (15 ml) was added dropwise a solution of methyl 12-hydroxydodecanoate (1.73 g, 7.5 mmol) in CH$_2$Cl$_2$ (7.5 ml) over 15 min. at 22° C. The reaction was stirred for an additional 10 min., diluted with ethyl ether (100 ml) and extracted with saturated aqueous NaCl (with 5% NaHCO$_3$, 4×75 ml). The ethyl ether layer was dried over Na$_2$SO$_4$, filtered, concentrated and distilled under vacuum to yield 1.4 g of the phosphoramidite in 60% yield; $^1$H NMR (CDCl$_3$) delta 3.65 (s, 3H), 3.39 (d, 3H), 2.32 (t, 2H), 1.22 (br s, 18H), 1.21 (d, 12H); $^{31}$P NMR (CH$_3$CN/C$_6$D$_6$) delta 148.9 with a minor (approximately 5%) contaminant at delta 10.7.

This phosphoramidite (0.20 g, 0.53 mmol) was oxidized with 15% t-butylhydroperoxide in CH$_3$OH (3.3 ml) and chromatographed to yield 0.19 g of the corresponding phosphoramidate in 95% yield: $^1$H NMR (CDCl$_3$) delta 3.87 (m, 1H), 3.65 (s, 3H), 3.64 (d, 3H) 2.27 (t, 2H), 1.28 (br s 18H), 1.21 (d, 12H); $^{31}$p NMR (CDCl$_3$) delta 10.23. Analysis calculated for C$_{20}$H$_{42}$O$_5$PN: C, 58.94, H, 10.39; p, 7.60: N, 3.44. Found: C, 58.78; H, 10.26; P, 7.82; N, 3.42.

Example II

Synthesis of 12-Phenyl-12-oxododecyl Methyl N-morpholino Phosphoramidite

12-Phenyl-12-oxododecylmethyl-N-morpholinophosphoramidite is shown below:

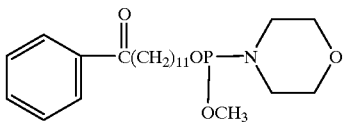

A. Preparation of 12-tertButyldimethylsiloxydodecanoic acid

A solution of 12-hydroxydodecanoic acid (2.1 g, 10 mmol) and tert-butyldimethylchlorosilane (3.74 g, 23 mmol), triethylamine (3.2 ml, 23 mmol), and dimethylaminopyridine (0.122 g, 1 mmol) in CH$_2$Cl$_2$ (50 ml) was stirred at 22° C. for 3 hours, concentrated on a rotary evaporator, diluted with ethyl ether (150 ml) and washed with 1M HCl (100 ml) and saturated aqueous NaCl (150 ml). The ethyl ether solution was concentrated under vacuum and dissolve din 1M KOH (20 ml) and THF (30 ml). The cloudy suspension was stirred rapidly at 22° C. for 3 min. upon which it became clear. It was then diluted with ethyl ether (150 ml) and washed as above. The ethyl ether solution was dried over Na$_2$SO$_4$, filtered, concentrated under vacuum, and chromatographed on silica gel (230–400 mesh) using as solvents: 1) 0.5% triethylamine and 15% ethyl acetate in hexanes, 2) 15% ethyl acetate in hexanes, and 3) 1% acetic acid and 15% ethyl acetate in hexanes to yield 12-tertbutyldimethylsiloxydodecanoic acid 3.16 g, in 96% yield: $^1$H NMR (CDCl$_3$) delta 7.95–7.35 (m, 5H), 3.65 (t, 2H), 2.34 (t, 2H), 1.27 (br s, 18H), 0.89 (s, 9H), 0.04 (s, 6H).

B. Preparation of 1-Phenyl-12-hydroxydodecanone

A phenyllithium solution (10 ml, 27 mmol) was added dropwise over 30 min. to a rapidly stirred solution of 12-tertbutyldimethylsiloxydodecanoic acid (3.16 g, 9.6 mmol) in THF (60 ml) at 0° C. with the formation of a white precipitate. The reaction mixture was then warmed to 23° (precipitate dissolved) and stirred for 5 hours. The reaction mixture was added dropwise in three aliquots to three (0° C.) hydrolyzing solutions prepared from 20 ml 1M HCl, 4 ml CH$_3$OH, and 16 ml H$_2$O. The product was extracted into ethyl acetate (2×100 ml) and washed with saturated aqueous NaHCO$_3$ followed by saturated aqueous NaCl, dried over Na$_2$SO$_4$, filtered, and concentrated in vacuo. To the crude silyl phenyl ketone (4.29 g) which was dissolved in THF (10 ml) was added tetrabutylammonium fluoride, (1M in THF, 22 ml). After this solution was stirred for 45 min. it was diluted with ethyl acetate (75 ml) and washed with 1 M HCl (100 ml), saturated aqueous NaHCO$_3$ (100 ml) dried over Na$_2$SO$_4$, filtered, and concentrated in vacuo. This crude product was crystallized from ethyl acetate/hexane to yield 1.89 g of 1-phenyl-12-hydroxydodecanone in 68% yield from hydroxydodecanoic acid: mp 68° C.; $^1$H NMR (CDCl$_3$) delta 7.95–7.35, (m, 5H), 3.62 (t, 2H), 2.95 (t, 2H), 1.28 (br s, 18H).

C. 12-Phenyl-12-oxo-dodecylmethyl-N-morpholinophosphoramidite

The 1-phenyl-12-hydroxydodecanone (0.772 g 2.8 mmol) was dried azeotropically with benzene (2×10 ml), dissolved in CH$_2$CL$_2$ (5 ml) and added dropwise over 5 min. under argon to a rapidly stirred solution of diisopropylethylamine (1.4 ml, 8 mmol) and N-morpholinochloromethoxyphosphine (0.77 ml, 4 mmol) in CH$_2$CL$_2$ (10 ml). The reaction was stirred another 15 min., diluted with (argon-sparged) ethyl acetate (75 ml), washed with saturated aqueous NaCl (with 5% NaHCO$_3$, 3×50 ml), and half saturated aqueous NaCl (50 ml), dried over Na$_2$SO$_4$, filtered, concentrated in vacuo and dried azeotropically with benzene (2×5 ml). The crude product was purified by chromatography on silica gel (230–400 mesh), by elution with 5% morpholine/15% ethyl acetate/80% hexanes to afford the desired phosphoramidite in 72% yield: $^1$H NMR (CDCl$_3$) 8.01–7.40 (m, 5H), 3.65–3.51 (m, 2H), 3.44 (d, 3H), 3.21–2.90 (m, 2H), 1.28 (br s, 18H); $^{31}$P NMR (CDCl$_3$) delta 143.9. The product is stable in CH$_2$Cl$_2$ or CH$_3$CN for at least 72 hours.

Example III

Synthesis of 5-Oxohexyl Methyl N,N-diisopropyl-phosphoramidite

5-Oxohexyl methyl N,N-diisopropyl-phosphoramidite is illustrated below:

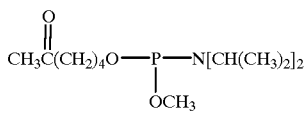

A. 5-Oxo-1-hexanol

A solution of 5-hexyne-1-ol (0.49 g, 5 mmol) in CH$_3$OH (5 ml) and H$_2$O (1ml) with mercurated Dowex 50 resin (See Newman, M. S., *J. Am. Chem. Soc.* (1953), 75, 4740–4742.) (0.6 g) was stirred slowly at room temperature for 18 hours. The solution was then filtered and the resin washed with CH$_3$OH (5 ml) and ethyl ether (30 ml). Water (10 ml) was added to the filtrate, the ethereal layer removed, and the aqueous layer washed with ethyl ether (30 ml). The combined ether layers were washed with saturated aqueous NaHCO$_3$ (50 ml) and saturated aqueous NaCl (50 ml), dried over Na$_2$SO$_4$, filtered, and concentrated in vacuo to yield 0.345 g of crude 5-oxo-1-hexanol (78%). The crude product was purified by chromatography in silica gel (230–400 mesh) with 5% CH$_3$OH in CH$_2$Cl$_2$: $^1$H NMR (CDCl$_3$) delta 3.63 (br m, 3H), 2.49 (t, 2H), 2.16 (s, 3H), 1.60 (br m, 4 H).

B. 5-Oxohexyl methyl N, N,-diisopropylphosphoramidite

To a rapidly stirred solution of diisopropylethylamine (2.3 ml, 13 mmol) and chlorodiisopropylaminomethoxyphosphine (1.4 ml, 6.5 mmol) in CH$_2$Cl$_2$ (15 ml) was added dropwise to a solution of 5-oxo-1-hexanol (0.58 g, 5 mmol) in CH$_2$CL$_2$ (7 ml) over 10 min. The reaction was stirred at room temperature for an additional 10 min, diluted with ethyl acetate (100 ml) and extracted with saturated aqueous NaCl (with 5% NaHCO$_3$5, 3×75 ml). The ethyl acetate layer was dried over MgSO$_4$, filtered, concentrated and distilled in vacuo to yield 0.65 g of the methyl ketone phosphoramidite (50%).

Example IV

Synthesis of 12-methyl-11,12-diacetyltridecanediol methyl N-mopholino phosphoramidite 12-Methyl-11,12-diacetyltridecanediol methyl N-mopholino phosphoramidite is illustrated below:

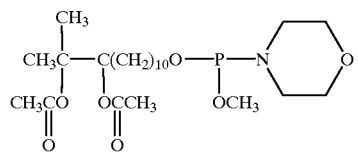

A. Methoxy-11-bromoundecane (1.33 g, 5 mmol) and triphenylphosphine (1.31 g, 5 mmol) are combined in dimethyl sulfoxide (5 ml) and allowed to stand at room temperature for 2 days.

In a separate flask, sodium hydride (5 mmol as suspension in mineral oil) is washed several times with n-pentane. Dimethyl sulfoxide (5 ml) is then added and the mixture heated at 75° for 45 min. (H$_2$ evolution ceases) to produce a 1M solution dimsylsodium. This dimsylsodium solution is cooled on an ice bath and the solution of the phosphonium salt (above) is added to it. The resulting mixture is stirred at room temperature for 10 min. and acetone (0.37 ml, 5 mmol) is added to it. The reaction is stirred at room temperature for 30 min. and the product is distilled directly from this solution under reduced pressure. See, for example, Greenwald, R., Chaykovsky, M., and Corey, E. J., *J. Org. Chem.* (1963) 28, 1128–1129; Cadogan, J. I. G. ed. *Organophosphorous Reagents in Organic Synthesis*, 1979 Academic Press; and Witting, G. & Schoellkopf, V. *Org. Syn. Coll.*, Vol. V, P. 751.

B. Thallium acetate (2.63 g, 10 mmol) is heated at reflux in dry acetic acid (7 ml) for 1 hr. To the cooled mixture are added 13-methoxy-2-methyl-2-tridecene (1.13 g, 5 mmol) and iodine (2.54 g, 5 mmol). This suspension is heated at reflux for 9 hr. with stirring and cooled to room temperature. The thallium iodide precipitate is removed by filtration and washed with ethyl ether. The filtrates are combined and concentrated by rotary evaporation. The residue is taken up in ethyl acetate (100 ml) and washed with saturated aqueous NaHCO$_3$ (2×100 ml) and saturated aqueous NaCl (100 ml), dried over MgSO$_4$, filtered, and concentrated in vacuo. The residue is purified by chromatography on silica gel. See, for example, Cambie, R. C. and Rutledge, P. S., *Org. Syn.*, (1979) 59, 169–176.

C. To a solution of 13-methoxy-2-methyl-2,3-tridecanediol diacetate (1.72 g, 5 mmol) in methylene chloride (25 ml) is added trimethylsilyl iodide (1 g, 5 mmol) and the resulting solution is stirred at room temperature for 8 hr. The solution is concentrated on a rotary evaporator, removing methylene chloride and methyl iodide. The residue is dissolved in ethyl acetate (100 ml) and shaken with saturated aqueous NaHCO$_3$ (100 ml) for 10 min. to hydrolyze the trimethylsilyl ether. The ethyl acetate layer is washed with water (100 ml) and saturated aqueous NaCl (100 ml), dried over MgSO$_4$, filtered, and concentrated in vacuo. The residue is purified by chromatography on silica gel if necessary. See, for example, Jung, M. E., Lyster, M. A., *J. Org. Chem.* (1977), 42, 3761–3764.

D. 12-Methyl-11,12-diacetyltridecanediol methyl N-morpholino phosphoramidite 12-methyl-11,12-diacetyl-1,11,12-tridecanetriol may be converted to its 1-(morpholino phosphoramidite) by a procedure analagous to that used to prepare the phenyl ketone morpholino phosphoramidite (supra). The crude product of this reaction may also be purified by chromatography on silica gel in the presence of morpholine.

Example V

Preparation of 12-Methylcarboxydodecyl 2-Chlorophenyl 2-Cyanoethyl Phosphate

12-Methylcarboxydodecyl 2-chlorophenyl 2-cyanoethyl phosphate is illustrated below:

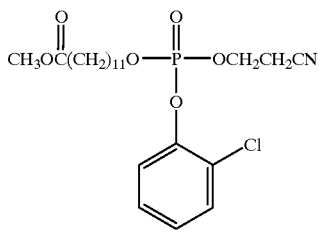

To a solution of triazole (1.52 g, 22 mmol) and triethylamine (3.10 ml, 22 mmol) in freshly distilled THF (70 ml) is added 2-chlorophenyl phosphorodichloridate. After 1 hour triethylammonium hydrochloride is filtered off and the filtrate containing 2-chlorophenyl phosphorodi(triazolide) is added to methyl 12-hydroxydodecanoate (2.31 g, 10 mmol) in distilled THF (10 ml). The reaction is stirred for about 6 hours and then 2-cyanoethanol (1.2 g, 16.5 mmol) is added and the stirring continued for an additional 18 hours. The reaction is evaporated to about 10 ml, diluted with ethyl acetate (100 ml) washed with 5% NaHCO$_3$ (3×50 ml) and H$_2$O (1×50 ml), dried over Na$_2$SO$_4$, filtered, concentrated in vacuo and dried azeotropically with benzene (2×25 ml). The crude product is purified in standard fashion by chromatography on silica gel by elution with mixtures of ethyl acetate in hexanes.

Example VI

Synthesis of Adapter Molecules

Polynucleotides were prepared on either an Applied Biosystems Model 380A or Beckman Instruments Systems 1 DNA Synthesizer. Synthesis programs were used as supplied. The linking agent was added to the polynucleotide either by the synthesizer using a modified program or manually as described below.
Adapter molecules d[HO$_2$C(CH$_2$)$_{11}$OpC-G-A-A-G-C-T-T-G-G-A-T-C-C-G-C]

(sometimes hereinafter referred to as acid 16-mer), d[CH$_3$CO(CH$_2$)$_4$OpC-G-A-A-G-C-T-T-G-G-A-T-C-C-G-C]

(sometimes hereinafter referred to as methyl ketone 16-mer), and d[PhCO(CH$_2$)$_{11}$OpC-G-A-A-G-C-T-T-G-G-A-T-G-G-G-C]

(sometimes hereinafter referred to as phenyl ketone 16-mer), were prepared by a combination of automated and manual solid phase methodologies, See e.g., Beaucage et al., supra; Matteucci et al., supra; Ti et al., supra; and Crockett, supra. The polynucleotide sequence was chosen to contain cleavage sites for two restriction endonucleases, HindIII and BamH1.

The fully protected unmodified hexadecanucleotide was prepared on a 1.0 or more commonly a 7.5 umole scale. With the automated procedure, a 0.2 M solution of the phosphoramidite described in Example I above in dry CH$_2$Cl$_2$ was loaded on the synthesizer and the program modified for the addition of this reagent after the detritylation of the last base. In the manual procedure, the support was removed from the synthesis column, dried in vacuo and treated as described below.

A. Synthesis of Acid 16-mer

Although automatically synthesized, deprotection of the fully protected dodecanoic acid hexadecanucleotide d[CH$_3$O$_2$C(CH$_2$)$_{11}$OpCpGpApApGpCpTpTpGpGpApT pCpCpGpC-cpg], was not carried out in the usual fashion because the standard scheme would generate the dodecanamide 16-mer d[NH$_2$CO(CH$_2$)$_{11}$OpC-G-A-A-G-C-T-T-G-G-A-T-C-C-G-C].

By inserting a trimethylamine/H$_2$O (7:1 v/v) treatment before the NH$_4$OH step the desired oligonucleotide was obtained and purified by HPLC to obtain d[HO$_2$C(CH$_2$)$_{11}$OpC-G-A-A-G-C-T-T-G-G-A-T-C-C-G-C].

After the fully protected dodecanoic acid hexadecanucleotide attached to controlled pore glass (8.5 umol) was removed from the columns, it was treated with thiophenol-:triethylamine:dioxane (1:2:2; 12 ml, 90 min) and then 12.5% trimethylamine in water (12 ml) for 48 hours at 37° C. evaporation and standard aqueous ammonia treatment afforded the crude acid 16-mer (713 A$_{260}$ units). Preparative HPLC purification gave pure acid 16-mer (130 A$_{260}$ units, 812 nmol; 9.6% yield based on starting 3'-nucleoside attached to the solid support). To characterize the acid 16-mer, it was digested to completion with snake venom phosphodiesterase and yielded, in the expected molar amounts, 12-hydroxydodecanoic acid and the four nucleosides. Nucleoside analysis. Theoretical: dA, 3.0; dG, 5.0; dC, 5.0; dT, 3.0. Found: dA, 3.0; dG, 5.0; dC, 5.1; dT, 2.9. C.

B. Methyl ketone 16-mer

The fully protected, unmodified hexadecanucleotide (approximately 9.5 umole) in a septum-capped centrifuge tube was rinsed with anhydrous acetonitrile and then reacted with phosphoramidite of Example III above (50 ul, approximately 200 umole) in anhydrous CH$_2$Cl$_2$ (475 ul) followed by 0.4 M tetrazole in acetonitrile (475 ul, 190 umol). After intermittent vortexing (15 min) the support was washed repeatedly with acetonitrile. Treatment with 0.1M iodine in THF:lutidine:H$_2$O (40:10:1) (1 ml, 100 umol) for 2 min, followed by washing with THF and acetonitrile yielded the fully protected methyl ketone 16-mer. Standard deprotection with thiophenol and concentrated aqueous ammonia yielded the crude product (1440 A$_{260}$ units) which was purified by preparative HPLC to yield 96.0 A$_{260}$ units (600 nmol) of ketone 16-mer (6.3% yield from starting 3'-nucleoside).

C. Phenyl ketone 16mer

With a manual procedure identical to that described above, the fully protected, unmodified hexadecanucleotide 16-mer (13 mg, approximately 0.7 umol) was reacted with phosphoramidite of Example II above (30 ul, approximately 70 umol). Preparative HPLC of the crude product (46 A$_{260}$ units) afforded 10.7 A$_{260}$ units (67 nmol) of phenyl ketone 16mer (approximately 10% from starting 3'-nucleoside) which was greater than 95% pure by gel electrophoretic and HPLC analyses.

D. Aldehyde 16-mer.

d[OHC(CH$_2$)$_{10}$O$_p$C-G-A-A-G-C-T-T-G-G-A-T-C-C-G-C]

The diacetyl diol phosphoramidite described in Example IV D above is added to the fully-protected, unmodified hexadecanucleotide by a procedure analagous to that used to prepare the phenyl ketone 16-mer. The standard aqueous ammonia treatment will remove the acetyl groups from the diol. Purification by HPLC will yield the diol 16-mer:

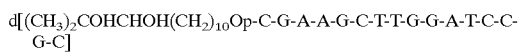
d[(CH$_3$)$_2$COHCHOH(CH$_2$)$_{10}$Op-C-G-A-A-G-C-T-T-G-G-A-T-C-C-G-C]

This compound is converted to the aldehyde polynucleotide by the following procedure (to be carried out just before attachment of the aldehyde polynucleotide to a preselected material).

The diol 16-mer (1 nmol.) is dissolved in sodium metaperiodate solution (20 ul, 20 mM, pH 4.5) and allowed to stand at room temperature for 30 min. Barium hydroxide (3.3 ul of a 150 mM solution) is added and the solution cooled on ice for 5 min. A small crystal of dry ice is then added and the solution is vortexed and centrifuged. The supernatant (22 ul) containing aldehyde 16-mer is removed, leaving behind the precipitate of barium iodate, barium periodate, and barium carbonate.

The yield of aldehyde 16-mer may be confirmed at this point by removing an aliquot for a brief reaction with 2,4 dinitrophenylhydrazine followed by HPLC analysis. The 2,4-DNP hydrazone of the aldehyde 16-mer is easily resolved from starting diol 16-mer by HPLC.

E. 3'-Carboxylic Acid 16-mer.

d[C-G-A-A-G-C-T-T-G-G-A-T-C-C-G-CpO(CH$_2$)$_{11}$CO$_2$H]

The 3'-carboxylic acid 16-mer is prepared by a standard solution phase phosphotriester method (See: Narang, S. A. Heiung, H. M. and Brousseau, R., *Methods Enzymol*, (1979) 68, 90–98) except that the starting 3'-residue is 4-N-benzoyl-2'-deoxycytidine-3'-O-(12-methylcarboxydodecyl, 2-chlorophenyl phosphate) instead of the 3'-O-benzoate analogue. Preparation of 5'-O-dimethoxy-trityl-4-N-benzoyl-2'-deoxycytidine-3'-O-(12-methylcarboxydodecyl, 2-chlorophenyl phosphate) is carried out in the following way. The phosphorylating agent described in Example V above (approximately 2.5 mmol) is dissolved in dry pyridine (25 ml) and treated with distilled triethylamine (3.7 ml, 27 mmol). After about 6 hours, the triethylammonium salt is formed and excess triethylamine is removed by evaporation with pyridine (3×25 ml). To this diester in dry pyridine (5 ml) is added 5'-O-dimethoxytrityl-4-N-benzoyl-2'-deoxycytidine (1.24 g, 2 mmol). This solution is concentrated and rendered anhydrous by addition and evaporation of dry pyridine (3×5 ml). Dry pyridine (5 ml), and 1-mesitylenesulphonyl-3-nitro-1, 2,4-triazole (2.27 g, 7.5 mmol) are added and the reaction stirred for about 30 minutes. The reaction is evaporated to about 1 ml, diluted with CH$_2$Cl$_2$ (20 ml), washed with 5% NaHCO$_3$ (3×10 ml) and H$_2$O (1×10 ml), dried over Na$_2$SO$_4$, filtered and concentrated in vacuo to yield the crude 3' nucleotide. This product is purified by chromatography on silica gel with 1–5% methanol in CH$_2$Cl$_2$:pyridine (99:1) as eluent. The chain assembly starts with the above described 3' modified nucleotide (about 0.5 mmol) and requires about five coupling steps with preformed di-, tri- and tetranucleotides. The coupling agent employed is 1-mesitylenesulphonyl-3-nitro-1,2,4-triazole and purification of products is achieved on either silica gel or reverse phase columns. The yield of the fully protected 3' modified carboxylic acid 16-mer is in the range of 0.04–0.07 mmol.

Treatment of the fully protected 3' modified carboxylic acid 16-mer (1 umol) with a solution of pyridine-2-carbaldoxime (19.5 mg, 160 umol) in dioxane/water (1:1, 375 ul) and 1,1,3,3-tetramethylguanidine (19 ul, 150 umol) at room temperature for 16–20 hours removes the 2-chlorophenyl protecting groups and converts the methyl ester into the carboxylic acid. After evaporation to dryness the residue is subjected to a standard aqueous ammonia treatment followed by a second evaporation to dryness. Treatment with 80% acetic acid (2.5 ml) for 30 minutes followed by addition of H$_2$O (2.5 ml) and extraction with diethyl ether (5×5 ml) affords the crude 3' carboxylic acid 16-mer (0.4–0.6 umol). This compound is purified in a fashion similar to that of the other adapter molecules. If necessary, the 5'-dimethoxytritylated 3' modified carboxylic acid 16-mer can be purified by preparative HPLC before the 80% acetic acid treatment.

Example VII

The Attachment of Small Molecules to the Acid 16-mer

A. Reaction with Biotin Hydrazide to form the Acyl-Biotinylated 16-mer

Acyl-biotinylated 16-mer is illustrated below:

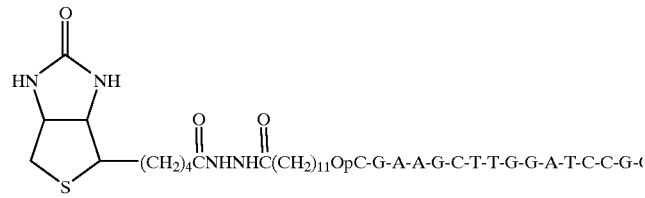

Acid 16-mer (3.0 A$_{260}$ units, 18 nmol) 1-ethyl-3-(3-dimethylaminopropyl) carbodiimide HCl (900 nmol, pH4) and biotin hydrazide (500 nmol) were combined (50 ul) and heated at 37° C. with shaking for 1 hour. The reaction mixture was chromatographed on a G-50 Sephadex column to afford 2.9 A$_{260}$ units of the acyl-biotinylated 16-mer (98%). HPLC analysis of the crude product showed that it was greater than 90% pure and contained a small amount of N-acyl urea 16-mer, an adduct of DEC with the acid 16-mer. Complete snake venom phosphodiesterase and bacterial alkaline phosphatase digestions of HPLC purified acyl-biotinylated 16-mer gave only the four nucleosides in the expected ratio, thus verifying that biotin hydrazide had not added to a base, i.e., cytosine. Nucleoside analysis: Theoretical: dA, 3.0; dG, 5.0; dC, 5.0; dT, 3.0. Found: dA, 2.7; dG, 5.0; dC, 4.8; dT, 2.7.

The [3'-$^{32}$P] acyl-biotinylated 16-mer was applied to an avidin-agarose column and washed with 1M NaCl/5× Denhardt's solution/20 mM Tris.HCl (pH8). As a control acid 16-mer was treated in an identical fashion. 93% of the labelled acyl-biotinylated 16-mer, as compared with 15% of acid 16-mer bound to the column.

B. Reaction with Aniline to Form Anilide 16-mer.

d[C$_6$H$_5$NHCO(CH$_2$)$_{11}$O$_p$C-G-A-A-G-C-T-T-G-G-A-T-C-C-G-C]

The reaction of acid 16-mer with aniline was carried out under conditions similar to those used in Example VII A, above. Acid 16-mer (1.0 A$_{260}$ unit, 6 nmol), 1-ethyl-3-(3-dimethylaminopropyl) carbodiimide.HCl (2.5 umol, pH6) and aniline hydrochloride solution (500 nmol, pH6) were combined (50 ul) and allowed to react for 12 hours. Gel electrophoretic analysis after gel filtration showed a single band corresponding to the anilide 16-mer with a mobility slightly slower than that of the starting acid 16-mer.

C. Reaction with N-Butyl Amine to form N-Butyl Amide 16-mer.

d[C$_4$H$_9$NHCO(CH$_2$)$_{11}$OpC-G-A-A-G-C-T-T-G-G-A-T-C-C-G-C]

Acid 16-mer (1.0 A$_{260}$ unit, 6 nmol), imidazole (5 umol), n-butylammonium hydrocloride (2.5 umol) and 1-ethyl-3-(-3-dimethylaminopropyl) carbodiimide hydrochloride (375 nmol) in H$_2$O (50 ul) at pH4 were allowed to react at room temperature for 2 hours. After chromatography on a G-5-0 Sephadex column, gel electrophoretic analysis on a 20% acrylamide/7M urea gel showed two bands corresponding to n-butyl amide 16-mer and acid 16-mer in an approximate ratio of 4:1. No band corresponding to N-acylurea 16-mer was detected.

It was found that imidazole significantly increased the yield of N-butyl amide 16-mer and greatly reduced the formation of the N-acylurea 16-mer. A similar increase in yield of N-butyl amide 16-mer was not observed when p-nitrophenol or N-hydroxysuccinimide was substituted for imidazole.

D. Reaction with Hydrazine to Form Hydrazide 16-mer.

d[NH$_2$NHCO(CH$_2$)$_{11}$OpC-G-A-A-G-C-T-T-G-G-A-T-C-C-G-C]

Acid 16mer (0.75 A$_{260}$ units, 4.5 nmol), DEC.HCl (250 nmole, pH 4.5) imidazole.HCl (2.5 umol, pH 4.1) and hydrazine (500 nmol) in H$_2$O (50 ul) were allowed to react for 2 hours at 37° C. The reaction mixture was chromatographed on a G-50 Sephadex column to afford 0.55 A$_{260}$ units of crude hydrazide 16-mer. Gel electrophoretic analysis showed one major band which was slower moving than that of the acid 16-mer.

Example VIII

Attachment of Small Molecules to the Methyl Ketone 16-mer and Phenylketone 16-mer Methyl ketone 16-mer is a preferred reagent for bond formation via the reductive amination procedure. (See Lane, C. F. *Synthesis*, (1975), 135–146).

A. Methyl biotinylated 16-mer

Methyl biotinylated 16-mer is illustrated below:

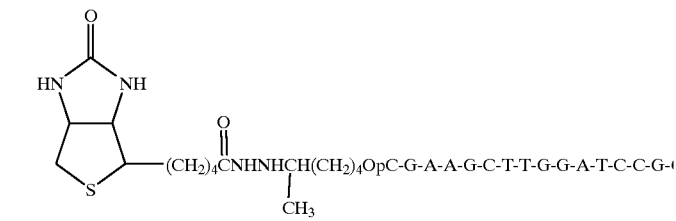

A solution of methyl ketone 16-mer (1.0 A$_{260}$ unit, 6 nmol), biotin hydrazide (250 nmol) and sodium cyanoborohydride (1.5 umol) was prepared in 0.05 M KH$_2$PO$_4$ 0.95 M KCl buffer (50 ul) at pH6.0 and allowed to react at room temperature for 4 hours. After gel filtration the DNA was analyzed by electrophoresis on a 20% polyacrylamide/7 M urea gel and showed two bands: the faster of which comigrated with that of the starting methyl ketone 16-mer (20%) while the slower corresponded to that of methyl biotinylated 16-mer (80%).

B. Methyl anilino 16-mer.

d[C$_6$H$_5$NHCH(CH$_3$(CH$_2$)$_4$OpC-G-A-A-G-C-T-T-G-G-A-T-C-C-G-C]

In a reaction identical to that described above except that aniline was substituted for biotin hydrizide, gel electrophoretic analysis showed two bands of equal intensity, the faster of which comigrated with methyl ketone 16-mer.

C. Phenyl biotinylated 16-mer.

Phenyl biotinylated 16-mer is illustrated below:

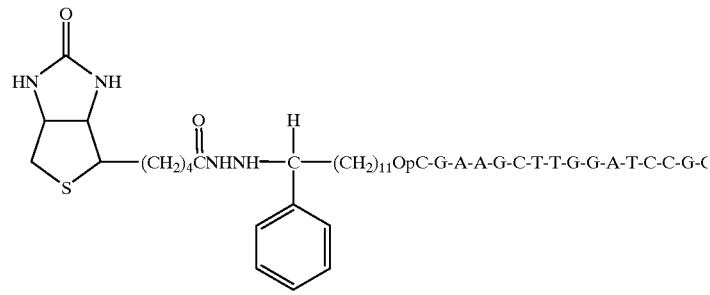

A mixture of phenyl ketone 16-mer (12 nmol, 2.0 $A_{260}$ units) biotin hydrazide (1 umol) and sodium cyanoborohydride (50 nmol) were combined in 50 mM potassium phosphate buffer (150 ul, pH 6.0) in sealed tubes and heated at 40° C. for 115 hours. After the reaction mixture was chromatographed on a G-50 sephadex column, the DNA was then electrophoresed on a 20% acrylamide/7M urea gel to afford two major bands of equal intensity, the faster of which comigrated with the starting material. The DNA was isolated from the slower band to afford 0.6 $A_{260}$ units of the phenyl biotinylated 16-mer (30%): HPLC analysis: greater than 90% pure. Complete snake venom phosphodiesterase followed by bacteral alkaline phosphatase digestion gave the four nucleosides in the expected ratio, thus verifying that biotin hydrazide had not added to a base i.e., cytidine. Phenyl biotinylated 16-mer was labelled with [alpha-$^{32}$P] dCTP and terminal transferase and shown to bind to an avidin-agarose column. As a control, the phenyl ketone 16-mer was treated in an identical fashion. 78% of the labeled phenyl biotinylated 16-mer as compared with 11% of the phenyl ketone 16-mer bound to the column.

Treatment of the unmodified 16-mer, d(C-G-A-A-G-C-T-T-G-G-A-T-C-C-G-C), for 48 hours under identical reductive coupling conditions afforded only starting material.

Example IX

A. Covalent attachment of acid 16-mer to Polybead™-aromatic amine microspheres

A mixture (50 ul) of Polybead™-aromatic amine microspheres obtained from Polysciences, Inc. (40 ul of 2.5% solids suspension, 0.18 micron particle size, 300 nmol of aromatic amine) acid 16-mer (1.0 $A_{260}$ units, 6 nmol), DEC.HCl (1.2 umol, pH 4) and imidazole.HCl (5 umole, pH 4) was allowed to react in a sonicated bath for 2 hours. To quantitate the amount of attachment, [3'-$^{32}$P] acid 16-mer (0.5 pmol, 14,000 Cerenkov cpm) was added to the reaction. Upon completion of the reaction the suspension was diluted with 50 mM $NaH_2PO_4$ (pH 6, 900 ul) and loaded onto a centrifugal filter containing a nylon 66 membrane and washed sequentially with the above phosphate buffer (900 ul, 2×), 1M $NaH_2PO_4$/0.05% SDS (900 ul, 1×) and 0.1M NaOH (900 ul, 1×). Cerenkov counting of the latex gave 1,600 cpm indicating that 11% of the acid 16-mer was covalently bound to the latex. As a control, a similar reaction to that described above, except that the carbodiimide was not included, was carried out. In this case, Cerenkov counting of the latex showed that less than 1% (100 cpm) of the acid 16-mer was associated with the latex.

B. Synthesis of hydrazide functionalized latex

Polybead™-carboxylate microparticles obtained from Polysciences, Inc. (1.5 ml of 2.5% suspension, 0.8 micron bead size, 3.7 umol of carboxylate) were washed with $H_2O$ and resuspended in 0.3M succinic acid dihydrazide (500 ul, 150 umol). To the slurry was added, 0.12M 1-ethyl-3-(3-dimethylaminopropyl) carbodiimide (500 ul, 50 umol) and the mixture was allowed to react for 1 hour. After the particles were centrifuged and washed with $H_2O$, they were subjected to a quantitative TNBS assay (Antoni, G. Presentini, R. and Neri, P., *Anal. Biochem.* (1983) 129, 60–63.) which showed a load of 20 umol hydrazide per gram.

C. Covalent attachment of acid 16-mer to Polybead™-hydrazide-microspheres

A mixture (50 ul) of the hydrazide derivatized latex beads (40 ul of 5% solution, 0.8 micron particle size, 60 nmol), acid 16-mer (1.0 $A_{260}$ units, 6 nmol) and DEC.HCl (1.2 umol, pH 4) was allowed to react for 2 hours. [3'-$^{32}$P] acid 16-mer (0.5 pmol), 8,900 Cerenkov cpm) was added to quantitate the amount of attachment. After washing the latex as described above, Cerenkov counting showed that 15% (1,300 cpm) of the acid 16-mer was covalently bound to the latex.

As a control, the methyl ketone 16-mer was treated exactly as described above. Cerenkov counting of the latex showed that approximately 2% (200 cpm) of the ketone 16-mer was associated with the latex indicating that attachment did not take place between residual carboxylates on the support and the exocyclic amines of the DNA bases.

Example X

Ligation of Acid 16-mer and 5'-Biotinylated 16-mer to Cloned DNA

The second polynucleotide that was ligated to the acid 16-mer or acyl biotinylated 16-mer was obtained from a single-stranded M13mp7 clone that contained approximately 1.1 kb of an albumin cDNA (See e.g. Lawn, R. M., Adelman, J., Bock, S. C., Franke, A. E., Houck, C. M., Najarian, R. C., Seeburg, P. H., Wion, K. L., *Nucleic Acids Res.* (1981) 9, 6103–6114.) inserted at the Pst restriction endonuclease site of the polylinker.

Figure 5:
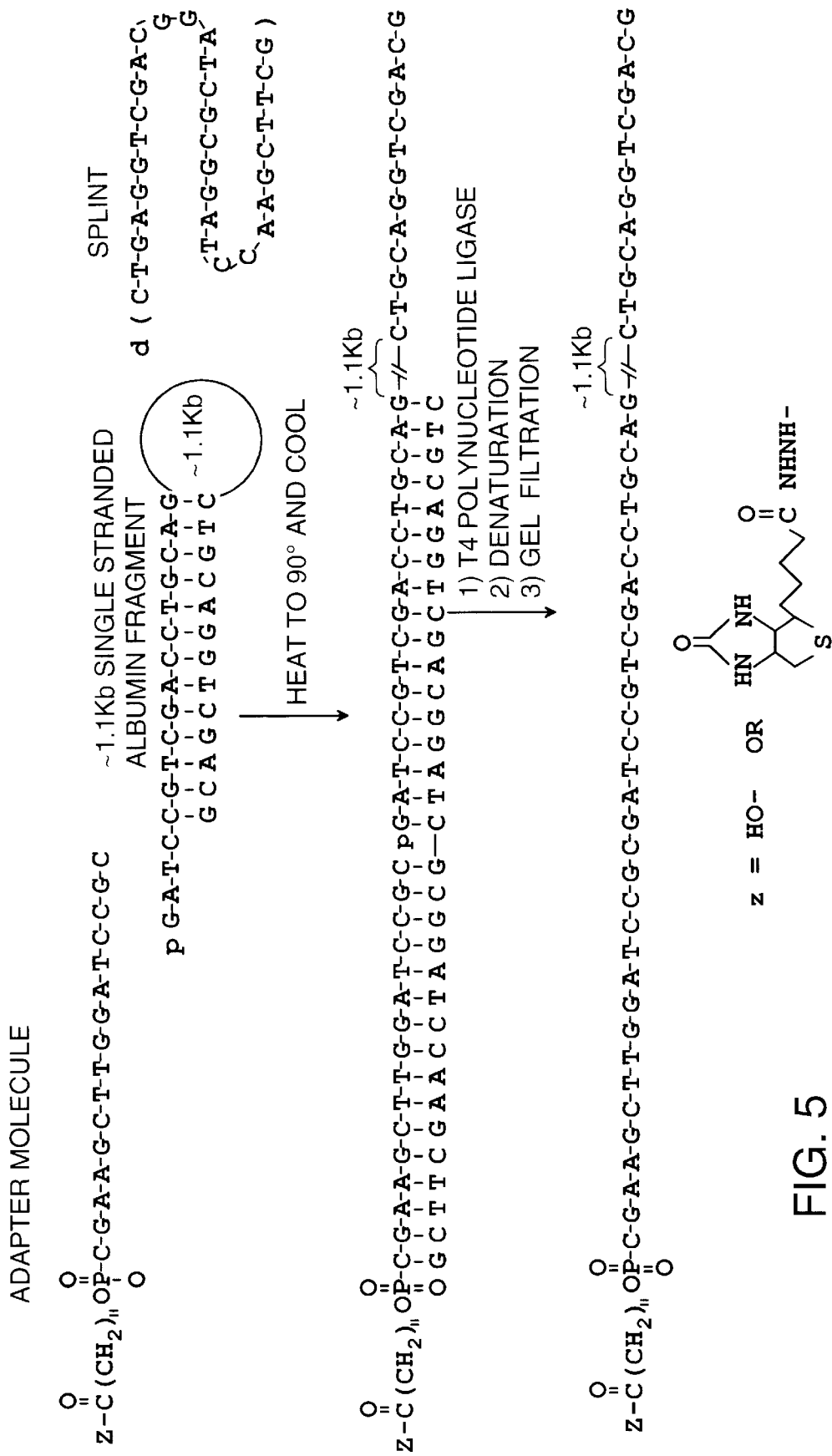
FIG. 5 is a schematic view of a ligation method for formation of a functionalized polynucleotide, e.g., 5'-biotinylated polynucleotide or 5'-carboxylic acid polynucleotide.

Because this polylinker consists of an inverted repeat, it can form a double-stranded region that can be cut with various restriction endonucleases (Ricca, G. A., Taylor, J. M. and Kalinyak, J. E., *Proc. Natl. Acad. Sci. USA* (1982) 79, 724–728). Digestion of this M13 clone with the BamH1 restriction enzyme gave a single-stranded albumin fragment which had the following sequence at its 5' end, 5' GATC-CGTCGACCTGCAG 3', see FIG. 5. The required oligonucleotide splint was chosen to be complementary to the 16-mer and the 5' end sequence of the albumin fragment and had the sequence d(CTGCAGGTCGACGGATCGCGGATCCAAGCTTCG). This 33-mer was prepared by standard polynucleotide synthesis methods.

A. Preparation of 5'-biotinylated polynucleotide

Figures 6, 7:
FIG. 6 is an autoradiogram of a polyacrylamide gel demonstrating the formation of the 5'-biotinylated polynucleotide (lane B) and the 5'-carboxylic acid polynucleotide (lane C) by ligation of the appropriate adapter molecule to the 1.1 kb fragment of albumin (lane A).
FIG. 7 is an autoradiogram of an agarose gel exemplifying the displacement polynucleotide assay shown in FIG. 1 with a latex-immobilized reagent complex. Section A (no target nucleotide sequence added) and Section B (added target nucleotide sequence) show the rate of the displacement reaction at 0 min. (lane 1), 12 min. (lane 2), 20 min (lane 3), and 45 min. (lane 4). Band I corresponds to the displaced labeled polynucleotide. The immobilized reagent complex remains at the origin.

A reaction mixture (25 ul) of acyl-biotinylated 16-mer (100 pmol), 5'-$^{32}$P] single-stranded albumin fragment (10 pmol), 33-mer splint (100 pmol) and Tris-HCl (pH 7.5, 625 nmol) were boiled for 3 minutes and then cooled ion ice. Additions of $MgCl_2$ (250 nmol), dithiothreitol (250 nmol), ATP (25 nmol) and T4 polynucleotide ligase (400 units) were made and the reaction incubated at 37° for 1 hour. After the reaction was stopped by boiling, gel electrophoretic analysis on a 5% acrylamide/8.1M urea gel showed two bands corresponding to the ligation product, the biotinylated polynucleotide, and the starting albumin fragment in an approximate ratio of 4:1 (FIG. 6, lane B).

The efficiency of the ligation was quantitated by absorbing an aliquot of the ligation reaction onto a bed of avidin-agarose. Thus, 1.5% of the total was combined with 1M NaCl/5× Denhardt's solution/10 mM Tris-HCl (pH 7.6) buffer and added to an avidin-agarose slurry (100 ul) which had been washed with the same buffer. After the mixture was shaken for two minutes, centrifuged and washed with the buffer (500 ul, 2×), it was found that the 88% of the DNA bound to the support. When the albumin fragment alone was treated in a similar fashion, 7% of the DNA bound to the avidin-agarose.

B. Preparation of 5'-acid polynucleotide

A mixture (100 ul) of acid 16-mer (1500 pmol), [5'-$^{32}$P] single-stranded albumin fragment (100 pmol), 33-mer splint (1500 pmol) was treated in a fashion similar to that described for preparation of the 5'-biotinylated polynucleotide. Gel electrophoretic analysis of the crude reaction mixture showed two bands corresponding to the carboxylic acid polynucleotide and the starting albumin fragment in an approximate ratio of 4:1 (FIG. 6, lane C). The crude product was extracted with phenol, ethanol precipitated, and passed through a Sepharose CL-4B column to afford the carboxylic acid polynucleotide. Treatment of an aliquot of this product with calf intestinal alkaline phosphatase showed that 80% of the radioactivity associated with the starting [5'-$^{32}$P] albumin fragment was resistant to conversion to inorganic phosphate.

Example XI

Covalent Attachment of Carboxylic Acid Polynucleotide to a Latex Support

A mixture (50 ul) of Polybead™-aromatic amine microspheres obtained from Polysciences, Inc. (40 ul of a 2.5% solids suspension, 0.18 micron particle size, 300 nmol of aromatic amine), carboxylic acid polynucleotide (13.5 pmole, 41,700 Cerenkov cpm), DEC.HCl (12 umol, pH 4) and imidazole.HCl (5 umol, pH4) was allowed to react 2 hours in a sonicated bath. A second batch of DEC.HCl (500 nmol) was added and the reaction was allowed to proceed an addition four hours. The latex was centrifuged and washed sequentially with 50 mM NaH$_2$PO$_4$ (pH 6)/0.05% SDS (1 ml, 3×), 0.1M NaOH (1 ml, 2×) and H$_2$O (1 ml, 3×). Cerenkov counting of the latex and then subtracting the counts associated with the control where no DEC.HCl had been added, gave 22,100 cpm indicating that 8.2 pmol (60%) of the carboxylic acid polynucleotide was covalently bound to the latex.

Example XII

Binding of Acyl-Biotinylated 16-mer to an Avidin-Alkaline Phosphatase Complex

[3'-$^{32}$P]-acyl-biotinylated 16-mer (30 pmol, 16,500 cpm), dodecanamide 16-mer described in Example VI A supra, (3 nmol) and avidin-alkaline phosphatase complex (19 pmol, 4.85 units) were combined in 500 ul of buffer (1.0 NaCl, 50 mM Tris.HCl, pH 7.5). After 5 minutes, the mixture was chromatographed on a Sephacryl S-200 column (1.5×50 cm, buffer as above). The enzyme activity (quantitative recovery) and 80% of the [3'-$^{32}$P]-biotinylated 16-mer coeluted and were cleanly separated from the unbound oligonucleotides as monitored by both UV absorbance (dodecanamide 16-mer) and radioactivity (acyl-biotinylated 16-mer).

Example XIII

Displacement Polynucleotide Assay Where Reagent Complex Is Immobilized on Latex ps Formation of reagent complex A hybridization reaction (400 ul) containing the latex immobilized polynucleotide (0.6 pmol) of Example XI above, the labeled polynucleotide, [5'-$^{32}$P] d(TCCTTTGCCTCAGCATAGTTTTTGCAAACATC) (0.05 pmol) and the hybridization buffer (0.5M NaCl, 10 mM EDTA, 10 mM NaH$_2$PO$_4$/Na$_2$HOP$_4$ (pH 6.8) and 0.1% SDS) was incubated at 50° for three hours. Any unhybridized labeled polynucleotide was removed by centrifugation and washing of the latex-immobilized reagent complex with the hybridization buffer that now contained 0.2 M NaCl. The washed reagent complex was resuspended in the above hybridization buffer (400 ul).

Displacement of the labeled polynucleotide

A complementary 1.25 kb albumin gene sequence (2 pmol) was added to an aliquot of the immobilized reagent complex (150 ul, 0.02 pmol) and incubated at 50°. This target nucleotide sequence was obtained from a single-stranded M13 clone which was digested with the restriction endonuclease Hae III to produce a linear fragment. To follow the rate of the displacement reaction, aliquots (10 ul) were removed at 0, 12, 20 and 45 minutes and analyzed on a 1.5% agarose gel. The results in FIG. 7, panel B showed that the displacement was more than half complete after 12 minutes and that when no target nucleotide sequence was added (FIG. 8, panel A), only a very low level of the free labeled polynucleotide was detected after 45 minutes.

Example XIV

Attachment of Aldehyde 16-mer

The solution of aldehyde 16-mer (1 nmol in 22 ul) is added to alkaline phosphatase (1 nmol) in 25 ul of a buffer containing sodium phosphate (100 mM, pH 6), and sodium cyanoborohydride (50 mM). After 4 hours reaction at room temperature the reaction solution is applied directly to a gel filtration column (e.g. Sephacryl S-200) to separate the DNA/enzyme conjugate from the unreacted starting materials.

Example XV

Synthesis of Polyethylene Glycol Acid 16-mer, d [HO$_2$CCH$_2$(—OCH$_2$CH$_2$—)~$_{25}$OpC-G-A-A-G-C-T-T-G-G-A-T-C-C-G-C]

A dilute (ca. 10 mg/ml solution of polyethylene glycol (PEG molecular weight 1000, ca. 25 monomer units long) in dichloromethane is prepared and dried overnight over molecular sieves. To this mixture is added ethyl bromoacetate (one molar equivalent) and the mixture is vigorously stirred at room temperature over potassium carbonate (previously dried in vacuo at 100° C.). The mixture is then filtered to remove potassium carbonate and potassium bromide and evaporated. To the residue is added an aqueous solution of triethylamine (2M) and the mixture is refluxed overnight with a good condenser. The solution at this point contains a mixture of HO-(PEG)-OH and the triethylammonium salts of HO-(PEG)-O—CH$_2$CO$_2$H and HO$_2$CCH$_2$—O-(PEG)-O—CH$_2$CO$_2$ H in a molar ratio of 1:2:1.

The reaction mixture is applied to a fine mesh anion exchange column (Amberlite AG1-X1, mesh 400) in the hydroxide form. The column is washed with distilled water until the washings have a pH less than 9. The washings contain HO-(PEG)-OH. Affixed to the column is a mixture of the salts of HO-(PEG)-O—CH$_2$CO$_2$H and HO$_2$CCH$_2$—O-(PEG)-O—CH$_2$CO$_2$H. The last two species are then eluted with 1N formic acid, and the eluant is rotoevaporated to give a mixture of HO-(PEG)-O—CH$_2$CO$_2$ H and HO$_2$CCH$_2$—O-(PEG)-O—CH$_2$CO$_2$H. Residual formic acid is removed with a vacuum pump.

The mixture of HO-(PEG)-O—CH$_2$CO$_2$H and HO$_2$CCH$_2$—O-(PEG)-O—CH$_2$CO$_2$H is then esterfied with absolute methanol in the presence of Dowex 50 ion exchange resin (sulfonic acid form) as catalyst. The reaction mixture is refluxed for 2 hours, filtered to remove the catalyst and evaporated. The resulting mixture contains HO-(PEG)-O—CH$_2$CO$_2$CH$_3$ and H$_3$CO$_2$CCH$_2$—O-(PEG)-O—CH$_2$CO$_2$CH$_3$ in a ratio of approximately 2:1.

With an adaptation of a procedure for in situ generation of phosphoramidites (Barone, A. D., Tang, J.-Y., and Caruthers, M. H. *Nucleic Acids Res.* (1984) 12, 4051–4061), the polyethylene glycol acid 16-mer is prepared. Thus the mixture of HO-(PEG)-O—CH$_2$CO$_2$CH$_3$ and H$_3$CO$_2$CCH$_2$—O-(PEG)-O—CH$_2$CO$_2$CH$_3$ is dissolved in anhydrous dichloromethane and chlorodiisopropylaminomethoxyphosphine (one molar equivalent) and the diisopropylamine salt of tetrazole (0.5 molar equivalent) are allowed to react under an argon atmosphere for 30 minutes. The unreacted H$_3$CO$_2$CCH$_2$—O-(PEG)-O—CH$_2$CO$_2$CH$_3$ is not deleterious to the following coupling procedure. To the fully protected, unmodified 16-mer on controlled-pore-glass in a septum-capped centrifuge tube flushed with argon is added 0.4M tetrazole in acetonitrile (40 molar equivalents) and the in situ generated PEG phosphoramidite (20 molar equivalents). After intermittent vortexing for 15 min. the support is washed repeated with acetonitrile. Treatment with 0.1M iodine in THF:lutidine:H$_2$O (40:10:1) for 2 min, followed by washing with THF and acetonitrile yields the fully protected polyethylene glycol acid methyl ester 16-mer attached to controlled-pore-glass. Deprotection and purification as described for the acid 16-mer affords the polyethylene glycol acid 16-mer.

It is understood that the examples and embodiments described herein are for illustrative purposes only and that various modifications or changes in light thereof that will be suggested to persons skilled in the art are to be included in the spirit and purview of this application and the scope of the approved claims.

We claim:

1. A method for attaching a polynucleotide to a preselected material selected from the group consisting of a solid support, an insoluble matrix, a protein, a small molecule, and a label which comprises:

(a) attaching a first polynucleotide, through its 5' or 3' end, to a linking agent represented by the formula

wherein R$_1$ is a functional moiety selected from the group consisting of —COOH, —CHO, a detectable moiety, an affinity agent, and a hapten, wherein n is an integer from 1 to 20, wherein for n>1, each of said R$_1$ may be a different selection from said group, R$_2$ is an aliphatic moiety, and R$_3$ is a phosphinylating or phosphorylating moiety represented by the formula

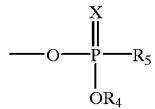

wherein R$_2$ is selected from the group consisting of methyl, cyanoethyl and chlorophenyl; R$_5$ is selected from the group consisting of morpholine, N,N-diisopropylamine and —OCH$_2$CH$_2$CN, and X is an oxygen atom, a sulfur atom or a pair of electrons;
   wherein R$_1$ and R$_2$ are stable to conditions of polynucleotide synthesis, wherein said first polynucleotide is attached to said liking agent via R$_3$ moiety, and wherein said first polynucleotide and said linking agent together form an adapter molecule;

(b) ligating said adapter molecule with a second polynucleotide, through the 5' or 3' end of said second polynucleotide to the 5' or 3' end of the first polynucleotide not attached to the adapter molecule, to form a functionalized polynucleotide; and (c) reacting said functionalized polynucleotide with said preselected material.

2. A method for attaching a polynucleotide to a preselected material selected from the group consisting of a solid support, an insoluble matrix, a protein, a small molecule, and a label which comprises:

(a) attaching a first polynucleotide, through its 5' or 3' end, to a linking agent represented by the formula

wherein R$_1$ is a functional group selected from the group consisting of —COOH, —CHO, a detectable moiety, an affinity agent, and a hapten, wherein n is an integer from 1 to 20, wherein for n>1, each of said R$_1$ may be a different selection from said group, R$_2$ is an aliphatic moiety, and R$_3$ is a phosphinylating or phosphorylating moiety represented by the formula

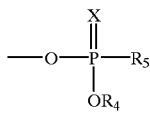

wherein R$_4$ is selected from the group consisting of methyl, cyanoethyl and chlorophenyl, R$_5$ is selected from the group consisting of morpholine, N,N-diisopropylamine and —OCH$_2$CH$_2$CN, and X is an oxygen atom, a sulfur atom or a pair of electrons;
   wherein R$_1$ and R$_2$ are stable to conditions of polynucleotide synthesis, wherein said first polynucleotide is attached to said linking agent via the R$_3$ group, and wherein said first polynucleotide and said linking agent together form an adapter molecule;

(b) reacting said adapter molecule with said preselected material; and (c) ligating said adapter molecule with a second polynucleotide, through the 5' or 3' end of said second polynucleotide to the 5' or 3' end of the first polynucleotide not attached to the adapter molecule.

3. A method for attaching a polynucleotide to a preselected material selected from the group consisting of a solid support, an insoluble matrix, a protein, a small molecule, and a label which comprises:

(a) attaching a first polynucleotide, through its 5' or 3' end, to a linking agent having a phosphoramidite or phosphate group, wherein said liking agent is selected from the group consisting of 12-methylcarboxyldodeclmethyl-N,N-diisopropylphosphoramidite;
   5-oxohexylmethyl-N,N-diisopropylphosphoramidite;
   12-phenyl-12-oxododecylmethyl-N-morpholinophosphoramidite;
   12-methyl-11,12-diacetyltridecanediol methyl N-morpholinosphoramadite;
   12-methylcarboxyldodecyl 2-chlorophenyl-2-cyanoethyl phosphate
   6-(biotinyloxy)hexyl-2-chlorophenyl-2-cyanoethyl phosphate; and
   penta(methyl-1-levulinyloxy)dipentaerythrityl-2-chlorophenyl 2-cyanoethyl phosphate;

wherein the linking agent is stable under conditions of polynucleotide synthesis, and wherein said first polynucleotide is attached to the linking agent via the phosphoramidite or phosphate group, and wherein said liking agent and said first polynucleotide together form an adapter molecule;

(b) reacting said adapter molecule with said preselected material; and (c) ligating said adapter molecule with a second polynucleotide through the 5' or 3' end of said second polynucleotide to the 5' or 3' end of the first polynucleotide not attached to the adapter molecule.

4. A method for attaching a polynucleotide to a preselected material selected from the group consisting of a solid support, an insoluble matrix, a protein, a small molecule, and a label which comprises:

(a) attaching a first polynucleotide, through its 5' or 3' end, to a linking agent having a phosphoramidite or phosphate group, wherein said linking agent is selected from the group consisting of 12-methylcarboxyldodecylmethyl-N,N-diisopropylphosphoramidite;
5-oxohexylmethyl-N,N-diisopropylphosphoramidite;
12-phenyl-12-oxododecylmethyl-N-morpholinophosphoramidite;
12-methyl-11,12-diacetyltridecanediol methyl N-morpholinophosphoramidite;
12-methylcarboxyldodecyl 2-chlorophenyl-2-cyanoethylphosphate; and
penta(methyl-1-levulinyloxy)dipentaerythrityl-2-chlorophenyl 2-cyanoethyl phosphate;

wherein said linking agent is stable under the condition of polynucleotide synthesis, wherein said first polynucleotide is attached to said linking agent via the phosphoramidite or phosphate group, and wherein said linking agent and said first polynucleotide together form an adapter molecule;

(b) ligating said adapter molecule with a second polynucleotide, through the 5' or 3' end of said second polynucleotide to the 5' or 3'0 end of the first polynucleotide not attached to the adapter molecule, to form a functionalized polynucleotide; and (c) reacting said functionalized polynucleotide with said preselected material.

5. The method of claim 1 or 2 wherein $R_1$ is a functional moiety selected from the group further consisting of biotinyl and combinations thereof.

* * * * *